(12) United States Patent
Huang et al.

(10) Patent No.: US 6,417,234 B1
(45) Date of Patent: *Jul. 9, 2002

(54) NORDIHYDROGUAIARETIC DERIVATIVES FOR USE IN TREATMENT OF TUMORS

(75) Inventors: Ru Chih C. Huang, Baltimore; Jonathan D. Heller, Dundalk, both of MD (US); Jih Ru Hwu; Ke Yung King, both of Hsinchu (TW)

(73) Assignee: Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/690,063

(22) Filed: Oct. 16, 2000

Related U.S. Application Data

(63) Continuation-in-part of application No. 09/418,594, filed on Oct. 15, 1999, now Pat. No. 6,214,874.

(51) Int. Cl.$^7$ ............................................... A61K 31/22
(52) U.S. Cl. ........................................................ 514/551
(58) Field of Search ......................................... 514/551

(56) References Cited

U.S. PATENT DOCUMENTS

| | | |
|---|---|---|
| 4,425,327 A | 1/1984 | Moller et al |
| 4,880,637 A | 11/1989 | Jordan |
| 5,008,294 A | 4/1991 | Jordan et al. |
| 5,559,149 A | 9/1996 | Clum et al. |
| 5,827,898 A | 10/1998 | Khandwala et al. |
| 5,837,252 A | 11/1998 | Sinnott et al. |
| 5,965,616 A | 10/1999 | Wang et al. |

OTHER PUBLICATIONS

Chen et al., Antiviral of Methylated Nordihydroguaiaretic Acids. 2. Targeting Herpes Simplex Virus Replication by the Mutation Insensitive Transcription Inhibitor Tetra–O–methyl–NDGA, Journal of Medicinal Chemistry, 1998, vol. 41, No. 16, pp. 3001–3007.

Gnabre et al., Isolation of Anti–HIV–1 Lignans from Larrea tridentata by Counter–Current Chromatography, Journal of Chromatography A., 719, 1995, pp. 1–12.

Gnabre et al., Characterization of Anti–HIV Lignans from Larrea tridentata, Tetrahedron, 1995, vol. 51, No. 45, pp. 12203–12210.

Gnabre et al., Inhibition of Human Immunodeficiency Virus Type 1 Transcription and Replication by DNA Sequence–Selective Plant Lignans, Proc. Natl. Acad. Sci. USA, 1995, vol. 92, pp. 11239–11243.

Gisvold et al., Lignans from Larrea divaricata, Journal of Pharmaceutical Sciences, 1974, vol. 63, No. 12, pp. 1905–1907.

Hwu et al., Antiviral Activities of Methylated Nordihydroguaiaretic Acids. 1. Synthesis, Structure Identification, and Inhibition of Tat–Regulated HIV Transactivation, J. Med. Chem., 1998, vol. 41, No. 16, pp. 2994–3000.

Huang et al., Regulation of HIV Promoter Activities in Human Embryonal Carcinoma Cells, NTERA–2, Gene Regulation and AIDS, 1989, pp. 147–160.

*Primary Examiner*—James H. Reamer
(74) *Attorney, Agent, or Firm*—Venable; Ann S. Hobbs

(57) ABSTRACT

Nordihydroguaiaretic acid derivatives and methods of use thereof for the treatment of tumors.

9 Claims, 20 Drawing Sheets

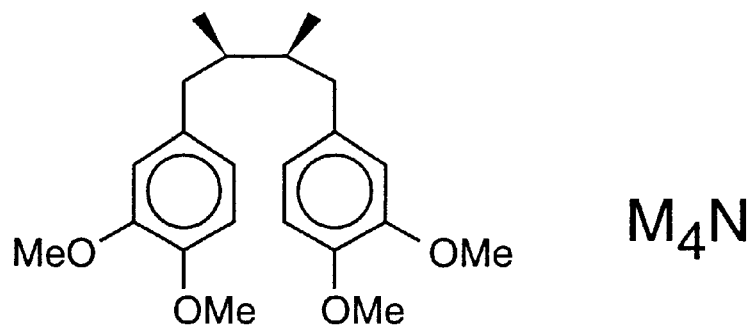
meso-1,4-Bis(3,4-dimethoxyphenyl)-(2R,3S)-dimethylbutane
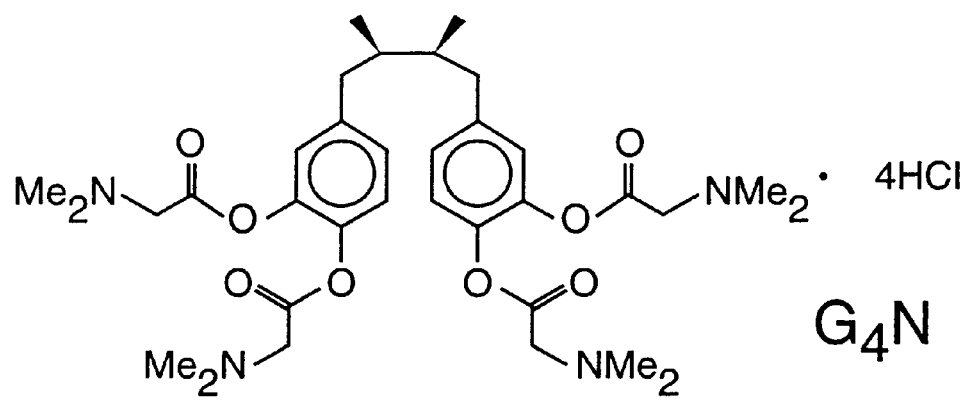
meso - 1,4 - Bis [3,4 - (dimethylaminoacetoxy)phenyl]- (2R,3S)-
dimethylbutane Hydrochloride Salt
FIG. I

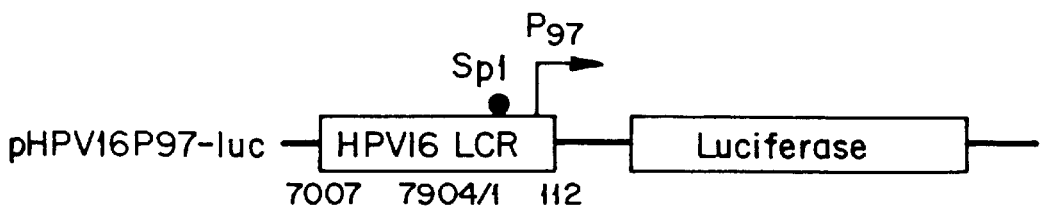
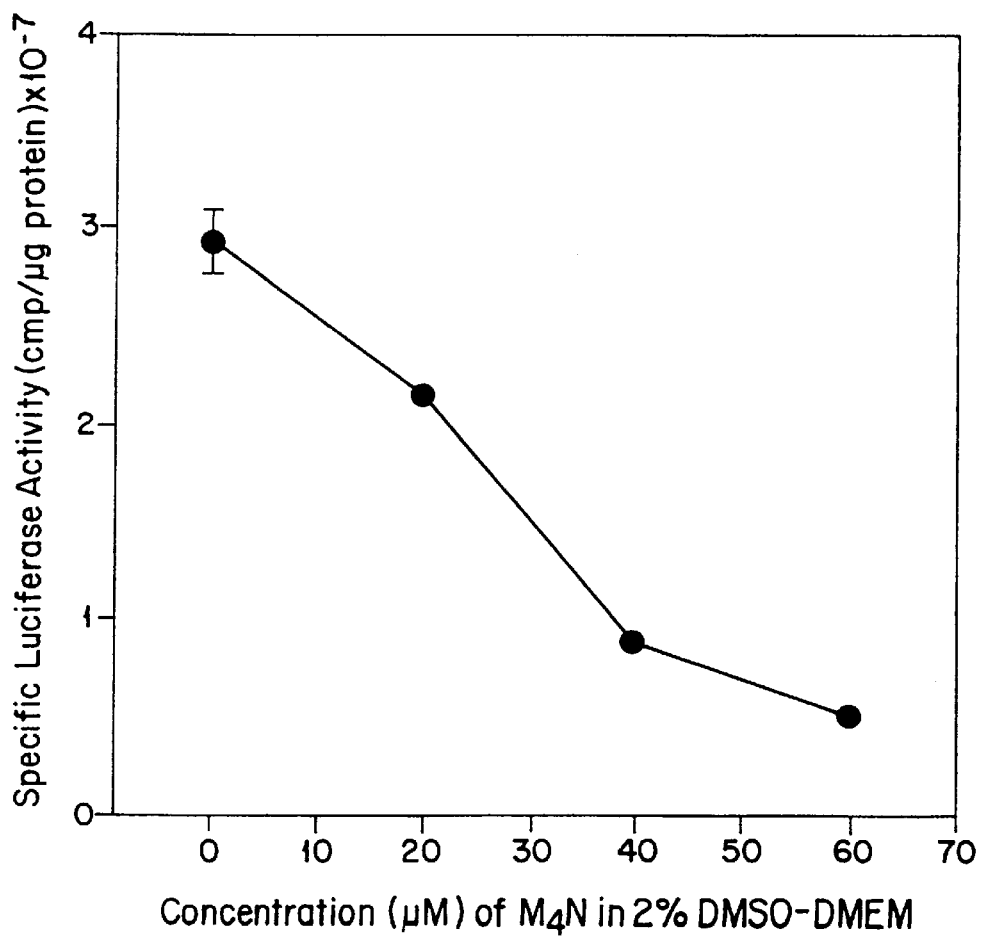
FIG. 2

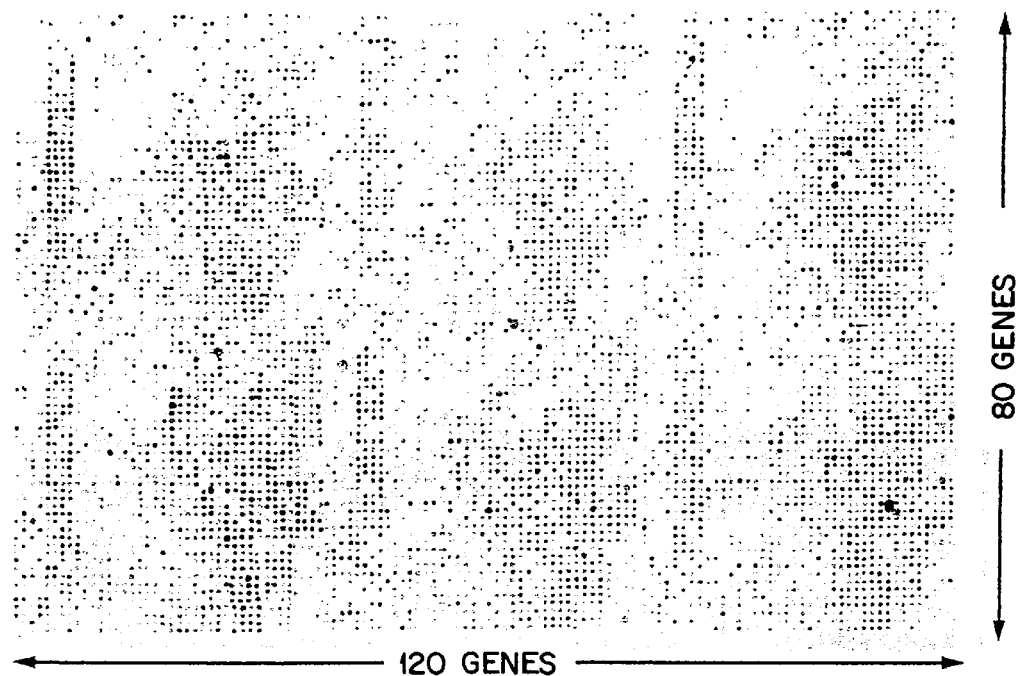
FIG. 5A  C3 DMSO
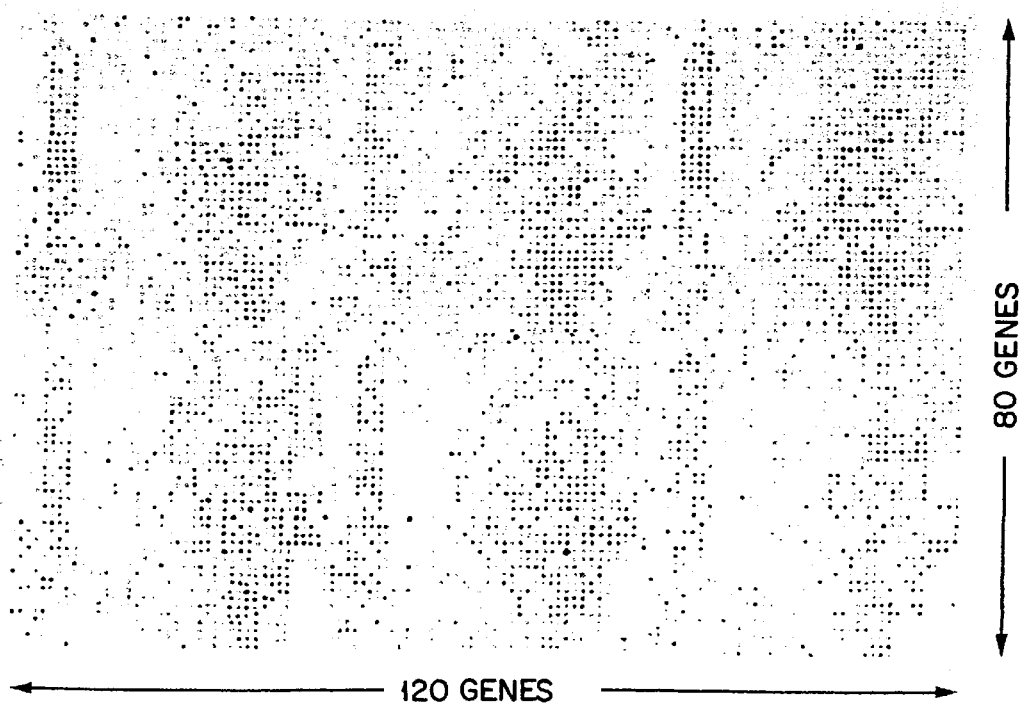
FIG. 5B  C3 M4N

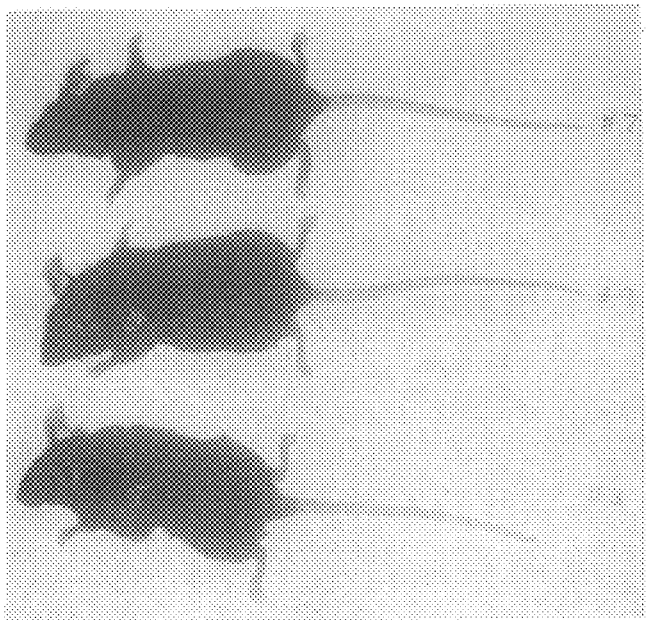
FIG. 6
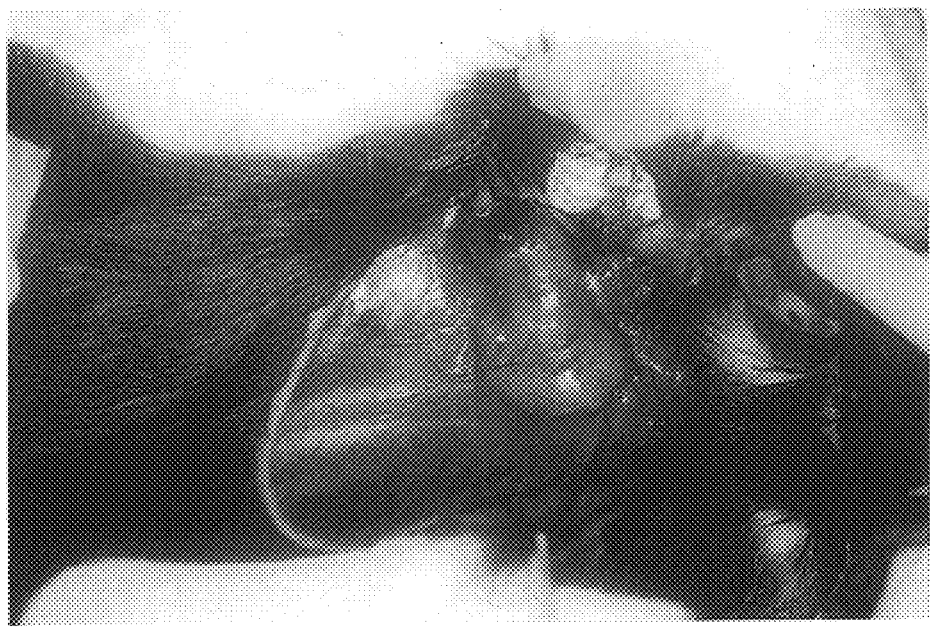

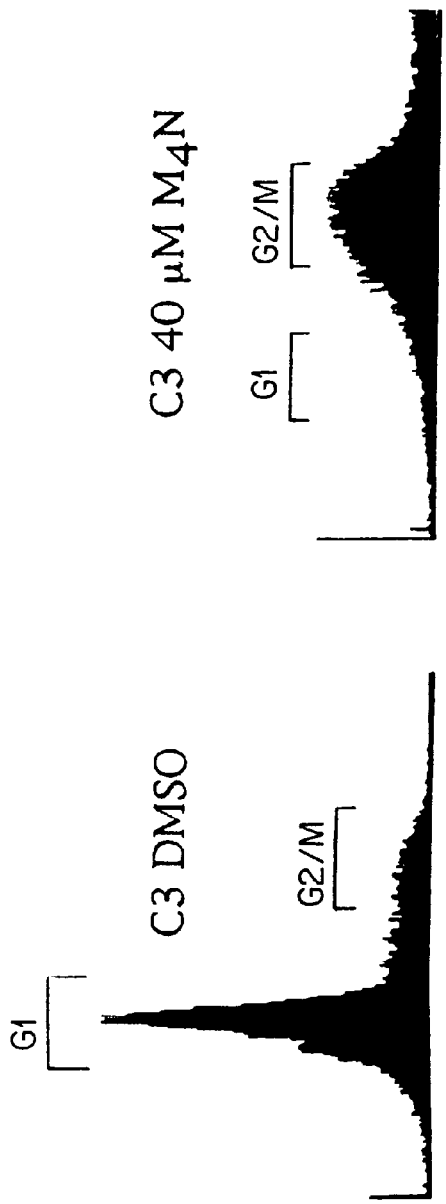
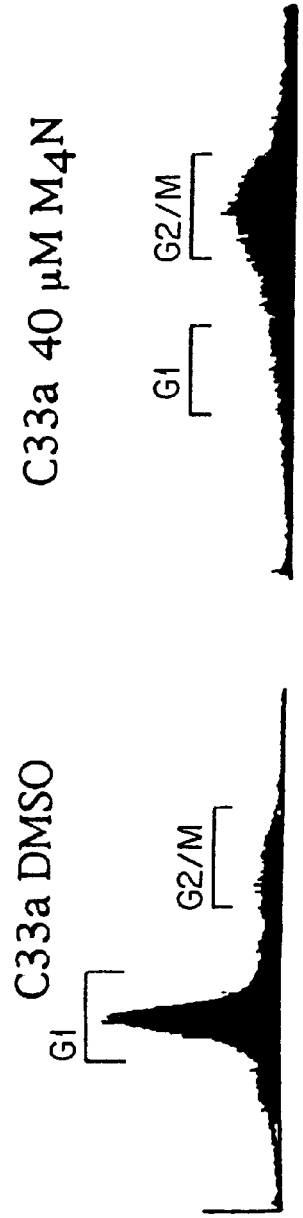
FIG. 10A
FIG. 10B

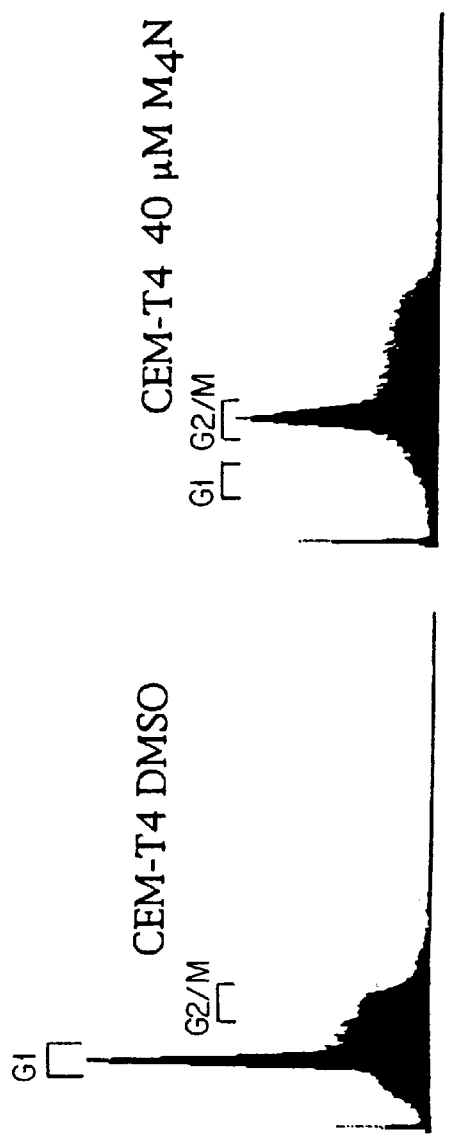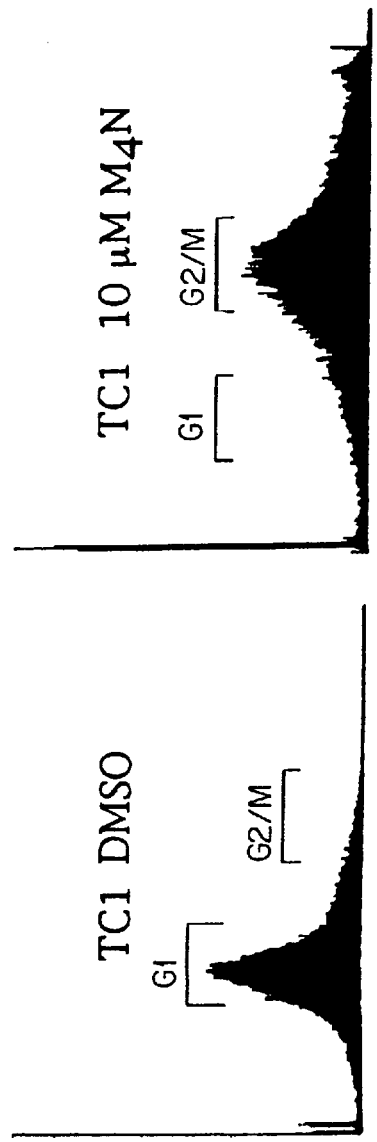
FIG. 10C
FIG. 10D

FIG. IIA
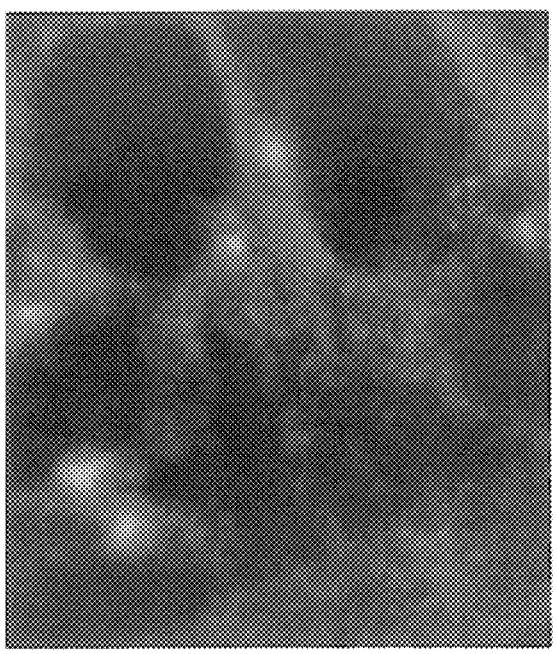 
Control　　　　　　　M4N Treated

Control    M4N Treated

NORDIHYDROGUAIARETIC DERIVATIVES FOR USE IN TREATMENT OF TUMORS

This application continuation-in-part to U.S. application Ser. No. 08/418,594, filed Oct. 15, 1999, now U.S. Pat. No. 6,214,874, which is hereby incorporated by reference.

The invention described and claimed herein was made in part under a grant from the National Institutes of Health. The U.S. Government has certain rights in the invention.

BACKGROUND OF THE INVENTION

1. Field of the Invention

The invention relates to the use of nordihydroguaiaretic acid derivatives, in particular derivatives containing substituents of naturally occuring amino acids, for the treatment of tumors and viral infections.

2. Background Information

Carcinogenesis is a multistage event affected by a variety of genetic and epigenetic factors and is typified by the outbreak of uncontrolled cell growth originated from different tissues. A universal goal for anticancer research lies in the development of a clinical treatment that is highly effective in curtailment of tumor growth, non-toxic to the host, and is affordable for most patients. Drugs that focus on the inhibition of targets that are unique to dividing cells should be effective chemotherapeutic agents without the risk of substantial side effects.

Cells pass through many checkpoints as they proceed through the cell cycle. Certain criteria must be met in order to pass each of these checkpoints. In the G2/M transition, the most essential regulator is the cyclin-dependent kinase CDC2. This kinase binds tightly to the regulatory protein cyclin B, and this complex, also called the maturation promoting factor (MPF), is responsible for stimulating a myriad of events that lead to the cell's entry into early prophase (1). Not surprisingly, the loss or deactivation of either component of the MPF will block cellular progression out of G2.

The expression and activity of the MPF is regulated at different levels. Cyclin B protein levels slowly rise through the G1 and S phases of the cell cycle, peak during the G2 to M phase transition, and drop sharply during mitosis (2). The CDC2 protein, on the other hand, is always present during the cell cycle, although levels rise slightly in the last stages of the G2 phase (3). The activity of the protein is dependent on the association with the appropriate cyclin, as well as on the dephosphorylation of its inhibitory sites by the phosphatase CDC25C (4,5). It has been shown that the failure of this dephosphorylation initiates G2 arrest in response to DNA damage by radiation or chemical action. Recent evidence also suggests that any remaining active CDC2 may be transported outside the nucleus following DNA damage (6).

A number of naturally occurring derivatives of the plant lignan nordihydroguaiaretic acid (NDGA) have been shown to block viral replication through the inhibition of viral transcription. This earlier work has shown that NDGA derivates, originally isolated from Larrea Tridentata and subsequently synthesized chemically, can inhibit the production of HIV (7,8), HSV (9), and HPV transcripts (10) by the deactivation of their Sp1-dependent promoters. Unexpectedly, one of these derivatives, tetra-O-methyl NDGA, appears to also induce cell cycle arrest in mammalian cell lines. The evidence presented hereinbelow demonstrates that $M_4N$ is capable of inducing G2 arrest in mammalian cells without detected toxicity, and supports the view that this arrest is due to the inhibition of the cyclin-dependent kinase CDC2.

Human papillomavirus (HPV) infection causes unregulated cell growth in many types of squamous epithelial cells, resulting in afflictions ranging from benign pallilomae (warts) to cervical, penile and mouth cancer. The strong association of these cancers with HPV and the widespread occurrence of infection denotes the importance of developing an anti HPV therapy.

Most, if not all, viruses, including those replicatively active mutants, are host dependent. They require the participation of certain cellular factors for supporting viral growth. Host cellular factors, unlike viral proteins, are not under mutational pressure and are in general, structurally invariable. Thus, compounds that block the usage of these cellular factors at different stages of the viral life cycle are likely to be good candidates as mutation insensitive antiviral drugs. Several studies using cellular factors as alternative targets for the inhibition of HIV-1 have been reviewed (11).

Applicants reported earlier that 3'-O-methylated NDGA (i.e. Mal.4), isolated from Creosote bush (Larrea tridentata) can specifically block basal HIV transcription, Tat-regulated transactivation, and HIV replication in human cell culture (12,13,14). Mal.4 exerts its effects by interfering with the binding of transcription factor Sp1 to the promoter of the HIV proviral template. The target of Mal.4 is mapped to nucleotides −87 to −40, the Sp1 binding sites of the HIV long terminal repeat (LTR). The unmodified NDGA, in vitro, does not inhibit HIV transcription and has no effect on Sp1 binding (12).

Isolation and purification of plant lignans, however, is labor intensive and costly. In anticipation of the possible clinical use of plant lignans in controlling Sp1-regulated viral and tumor growth in humans, nine different methylated NDGA activities were synthesized chemically using unmethylated NDGA as the parent substrate in large quantities with low cost (15). At drug concentrations below 30 $\mu$M, tetra-O-methyl NDGA was found to be most effective in the control of replication HIV via inhibition of Sp1 regulated proviral transcription and transactivation (15). This study has since been extended to the control of the growth of Herpes simplex virus (HSV-1 and HSV-2) (16). Herpes simplex immediate early (IE) ICP4 gene is essential for HSV replication (17). Its promoter region possesses eight Sp1 consensus binding sites (18), five of which are required for ICP4 gene expression. It thus makes the ICP4 gene a good candidate for such testing. Applicants have found that both 3-O-methyl NDGA (Mal. 4) and tetra-O-methyl NDGA ($M_4N$) are effective transcriptional inhibitors for HSV ICP4 gene expression in Vero cells via the blocking of Sp1 protein binding to the ICP4 promoter as shown by the electrophoretic mobility shift assay (16).

When the anti-HSV activities of $M_4N$ and Mal. 4 were tested and compared to that of acycloguanosine (acyclovir, ACV) in infected Vero cells, Applicants observed that the $IC_{50}$ for $M_4N$ varied between 11.7 $\mu$M to 4 $\mu$M for 10 passages of HSV-1 and 4 passages of HSV-2 without obvious uprising trend for requirement of higher drug concentration. However, the $IC_{50}$ for ACV increased from 7 $\mu$M for the first viral passage to 444 $\mu$M for the tenth passage of HSV-1 and to >88 $\mu$M for the fourth passage of HSV-2 indicating their rapid build-up of drug resistance against ACV in Vero cells. Consequently, while the selective index, S.I. ($TC_{50}/IC_{50}$) remained relatively stable for $M_4N$, the S.I. for ACV dropped 60 fold following the viral passages in Vero cells (16). Thus $M_4N$ is a mutation insensitive drug. It can inhibit ACV resistant HSV effectively (16).

Due to the fact that Sp1 is an important cellular transcription factor (19), the possible inhibitory effect of this class of compounds on the expression of Sp1-regulated cellular genes should be addressed. Mal.4 cannot displace Sp1 once it is stably bound to its binding sites (12). It therefore seemed likely that NDGA derivatives would have a greater effect on Sp1-regulated genes in proliferating cells than on the expression of Sp1-regulated housekeeping genes in stationary cells. In the former case, the drug will be able to compete with Sp1 protein for the Sp1 sites in gene promoters during DNA synthesis, while in the latter case, the drug may have little effect on the transcribing chromatin of housekeeping genes with Sp1 protein already stably bound at their promoters. This, in fact, has been shown to be the case. As will be demonstrated below, by using gene array studies with 9600 expressed genes, Applicants found products of most Sp1 regulated genes remained at similar levels, and not affected by the drug treatment of cervical cancer cells C3 in culture (FIG. 5). Even so, the relatively low selective index of $M_4N$ certainly limits its use to the lowest effective concentration if the drug must be used systemically. On the other hand, human papilloma virus induces solid cervical and oral tumors initially through the Sp1 regulated expression of HPV $E_6/E_7$ genes (20). Applicants reasoned that if drug can be delivered in situ, and be kept only in the tumor area, the drugs of high concentration may be used to effectively destroy the tumor with little damage to the patients.

SUMMARY OF THE INVENTION

Accordingly, it is one object of the invention to provide compounds and compositions for use in the treatment of cancerous and noncancerous tumors in animals, particularly in mammals, and most particularly in humans. According to this aspect of the invention, novel nordihydroguaiaretic acid derivatives are provided that inhibit tumor growth.

By nordihydroguaiaretic acid derivatives is meant compounds of the structure

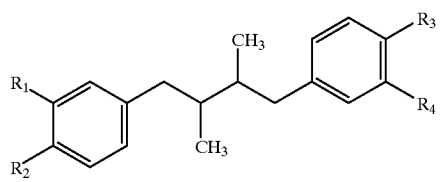

wherein $R_1$, $R_2$, $R_3$ and $R_4$ independently represent —OH, —OCH$_3$, —O(C=O)CH$_3$, or an amino acid residue, but are not each —OH, simultaneously. Amino acid substituents are intended to include, inter alia, alanine, arginine, asparagine, aspartate, cysteine, glutamate, gluamine, glycine, histidine, isoleucine, leucine, lysine, methionine, phenylalanine, proline, serine, threonine, tryptophan, tyrosine, valine, 5-hydroxylysine, 4-hydroxyproline, thyroxine, 3-methylhistidine, ε-N-methyllysine, ε-N,N,N-trimethyllysine, aminoadipic acid, γ-carboxyglutamic acid, phosphoserine, phosphothreonine, phosphotyrosine, N-methylarginine, and N-acetyllysine.

Particularly preferred compounds for use according to the invention are $M_4N$ and $G_4N$, which are shown in FIG. 1.

It is a further object of the invention to provide a method for treating cancerous and noncancerous tumors by the use of these novel derivatives, and by similar derivatives that were known in the art, but have not heretofore been used for the treatment of tumors. The method should be especially effective against rapidly proliferating cell types containing the cyclin dependent kinase CDC2. It is a further object of the invention to provide a method of inhibiting CDC2 in a eukaryotic cell cycle, particularly in an animal cell, more particularly in a mammalian cell, and most particularly in a human cell.

Tumors to be treated include any tumor that is sensitive to the above-mentioned compounds used according to the methods of the invention. In particular, this includes rapidly dividing cancerous and benign tumors that are sensitive to inhibition of the cyclin-dependent kinase CDC2 cycle.

The term "cancerous tumor" is intended to include any malignant tumor that may or may not have undergone metastasis. The term "noncancerous tumor" is intended to include any benign tumor. These terms are used as customarily understood by persons of skill in the art.

Examples of benign and malignant tumors which may be treated by the compositions and methods of the invention can be found in Table 1-1 of Cancer Biology (Raymond W. Ruddon, Cancer Biology, $3^{rd}$ Ed., Oxford Univ. Press, 1995, incorporated herein by reference). Tumors to be treated include those that are known to be of viral origin, as well as those that are not of viral origin. The compositions and methods of the invention are expected to be particularly useful in the treatment of solid tumors.

It is yet another object of the invention to provide a method of inhibiting the cyclin-dependent kinase CDC2 cycle. This method will be useful in inhibiting cell proliferation, particularly in rapidly dividing cell types.

In a preferred embodiment, the compounds and compositions described herein are used in the treatment of HPV-induced tumors. HPV-induced tumors include in particular, but are not limited to, cervical, oral, penile and head and neck cancers that are associated with HPV infection. The method comprises local application of nordihydroguaiaretic acid derivatives, in particular tetra-O-methyl nordihydroguaiaretic acid ($M_4N$) and tetraglycinal nordihydroguaiaretic acid ($G_4N$), to cancerous and non-cancerous HPV-induced tumors.

It is yet another object of the invention to provide a method of inhibiting viral replication and growth by the administration of the compounds of formula I containing amino acid substituents. Preferred for use in this method are compounds in which the amino acid substituents $R_1$, $R_2$, $R_3$ and $R_4$ are identical.

It is contemplated that $M_4N$, $G_4N$ and other derivatives will be administered by local injection into the tumors, generally along with pharmaceutically acceptable diluents, excipients and carriers. In preferred embodiments, $M_4N$ is injected into tumors in the form of a DMSO solution, and $G_4N$ is administered in PBS solution. The use of $G_4N$ will complement the use of $M_4N$, particularly in larger tumors (>2 cm$^3$), due to its water solubility, which allows it to spread to a larger region of the tumor. Other water-soluble and water-insoluble nordihydroguaiaretic acid derivatives can be similarly employed, according to the invention. These may also be employed in lipid based formulations for systemic delivery, as known and used in the art.

By pharmaceutically acceptable diluents, excipients and carriers is meant such compounds as will be known to persons of skill in the art as being compatible with $M_4N$, $G_4N$ and other similar derivatives and suitable for local administration to a human or other mammal according to the invention. Although the examples hereinbelow describe administration by means of local injection, other means of local administration, such as topical application or targeted delivery to the tumor site, may also be used.

The amount of compound administered to obtain the desired treatment effect will vary but can be readily determined by persons of skill in the art. The amount of dosage, frequency of administration, and length of treatment are dependent on the circumstances, primarily on the size and type of tumor. However, dosages of from 10 mg to 20 mg of either $M_4N$ alone or with similar amounts of $G_4N$ per gram tumor weight at intervals from daily to weekly or less frequently may be mentioned for purposes of illustration. Administration of 50 μl to 100 μl of $M_4N$ dissolved in DMSO at a concentration of 200 mg/ml, either alone or in combination with $G_4N$, is expected to be effective in many cases for tumors of 1–1.5 cm³.

BRIEF DESCRIPTION OF THE DRAWINGS

FIG. 1. Structures of $M_4N$ and $G_4N$

FIG. 2 Top. HPV-16 LCR showing region of $E_6/E_7$ promoter (pPV16P97) and the binding site for Sp1 protein.

FIG. 2 Bottom. The effect of $M_4N$ on the $E_6/E_7$ promoter activity in C-33A cells. (Inhibition of $E_6/E_7$ promoter driven luciferase gene transcription by different concentration of $M_4N$)

FIGS. 5A–5B. Effect of $M_4N$ on gene expression in C3 cells as examined by the GENE Assay analysis. 5A. GENE expressed in C3 cells after >2 hours of DMSA treatment (C3 DMSO). 5B. GENE expressed in C3 cells after >2 hours of $M_4N$ treatment using DMSO as solvent (C3 $M_4N$).

FIG. 6. Visual observations of tumor-bearing mice following $M_4N$ treatment. 6A. Mice bearing single tumors were treated with in situ injection of DMSO (#3) or $M_4N$ (#7). In situ injection of $M_4N$ was also made to one of the two tumors grown in mouse #9. 6B. $M_4N$ treated tumor (white scar) with untreated tumor from the same mouse, #9 as described in Table 2.

First column from the panel presnts the large size of tumors from mouse #4, 10, 12, following DMSO treatment (CON) as compared to the relatively small drug treated ($M_4N$ or $M_4N/G_4N$) lesions from mouse #12, 10, 27 and 20($M_4N$). The subsequent photographs are examples of these tumors examined at 100× magnification (A, B, C, DMSO treated, D untreated, E, F, G, H, $M_4N$ or $M_4N/G_4N$ treated) mice (Table 1 and Table 2).

Figure 8:
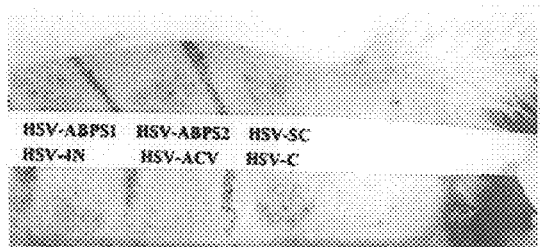

FIG. 8. HSV-1 replication in the absence of drugs (HSV-C, HSV-SC), in the presence of ineffective drugs ($ABDS_1$ ["HSV-$ABDS_1$"], $ABDS_2$ ["HSV-$ABDS_2$"]) and in the presence of effective drugs ($M_4N$ ["HSV-4N"] and ACV ["HSV-ACV"]).

FIG. 9. $M_4N$ Causes Growth Arrest in Mammalian Cells. (a–d) C3, CEM-T4, C33a, and TC-1 cells were treated with different concentrations of $M_4N$. The number of cells present at the initiation of the experiment is indicated as Day 0. After three days the number of viable cells were counted and plotted versus the $M_4N$ concentration. (e) C3 cells were split into T-25 flasks with 5×10³ cells per flask and given either $M_4N$ in 1% DMSO in media or 1% DMSO in media alone (first media change). After 3 days, one-half of the $M_4N$ treated cells were given fresh media containing only 1% DMSO (M-D), while the rest of the cells were given fresh media with the same conditions (second media change). The cells were counted daily and plotted versus the time of treatment.

FIG. 10. Cells Treated With $M_4N$ Arrest in G2/M. C3 cells (a), C33a cells (b), CEM-T4 cells (c), and TC1 cells (d) were grown for three days in media containing either 1% DMSO or 1% DMSO with $M_4N$ ($M_4N$). The cells were trypsinized, fixed with ethanol, stained with propidium iodide, and were subsequently analyzed by flow cytommetry. The data is displayed as number of cells (3–5×10⁴ total cells) versus propidium iodide stain intensity. The indicated stages of the cell cycle are labeled and correspond to the relative cellular DNA compliment as determined by staining intensity.

Figure 11B:
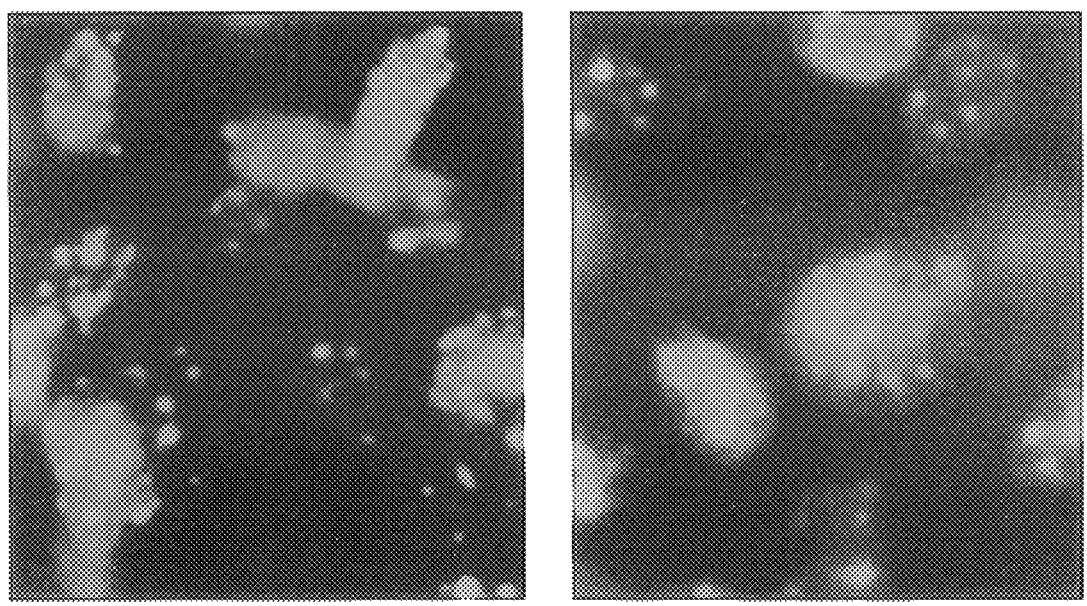

FIG. 11. C3 Cells Treated With 40 μM $M_4N$ Demonstrate G2 Cell Structures. C3 cells were grown on coverslips for three days in media containing either 1% DMSO (Control) or 1% DMSO with 40 μM $M_4N$ ($M_4N$). Samples were fixed with ethanol and incubated with antibodies against α (green) and γorange) tubulin (a) or with the DAPI DNA stain (b). Cells were examined by flourescence microscopy.

FIG. 12. CDC2 and Viral Oncogenes are Reduced by $M_4N$. C3 cells were grown for different amounts of time (numbers are in hours) in media containing either 1% DMSO (D) or 1% DMSO with 40 μM $M_4N$ (M). After the specified times, total protein or total RNA was isolated from the cells. Western blots (a—top two panels) were performed using antibodies against CDC2 or cyclin B with the same nitrocellulose filter. Kinase assays (a—bottom two panels) were performed, following immunoprecipitation with antibodies to cyclin B, by incubation with γ-³²P ATP and histone H1. The coomassie stain of the PAGE gel is included as control for loading. Kinase assays for 24 and 72 hour drug treatments were performed separately.

Northern blots (b) were performed on total RNA extracts. Filters were incubated overnight with random-primed ³²P-labeled DNA for CDC2 or GAPDH, washed, and exposed to film for three days. The same filter was used to test CDC2 and GAPDH RNA.

rtPCR analysis (c) was performed on total RNA extracts with primers hybridizing to regions within either HPV-16 E7 or GAPDH. Both primer pairs were used in the same reactions, and the products were analyzed by agarose gel electrophoresis.

Figures 13A, 13B, 13C:
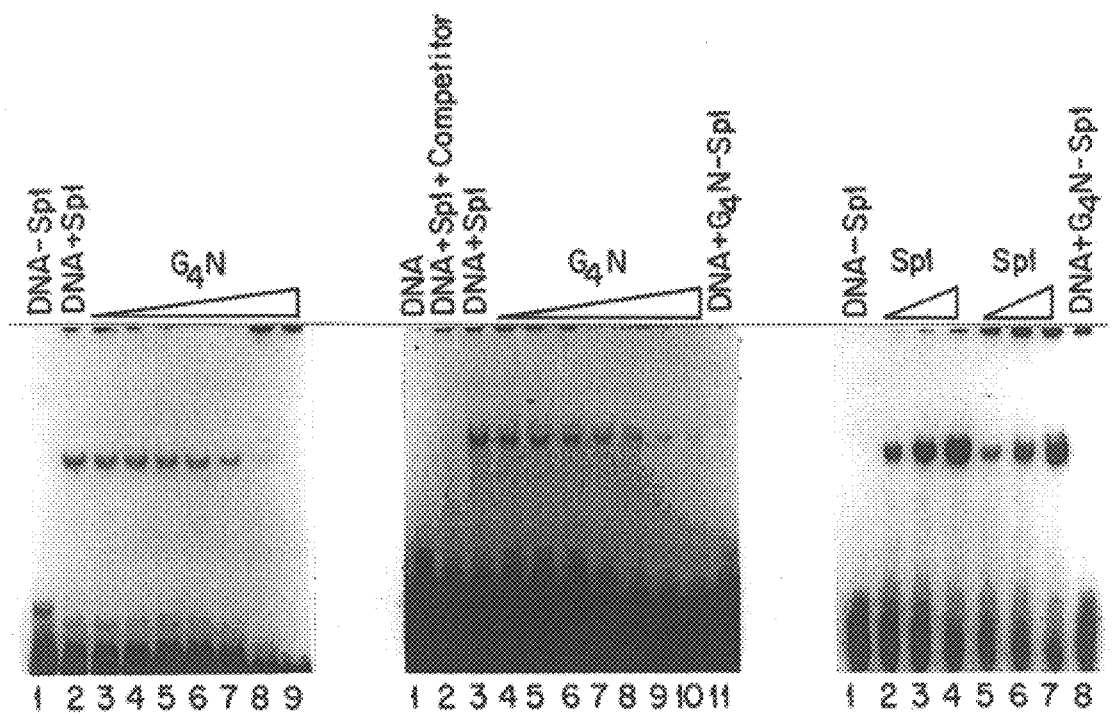
Figure 13D:
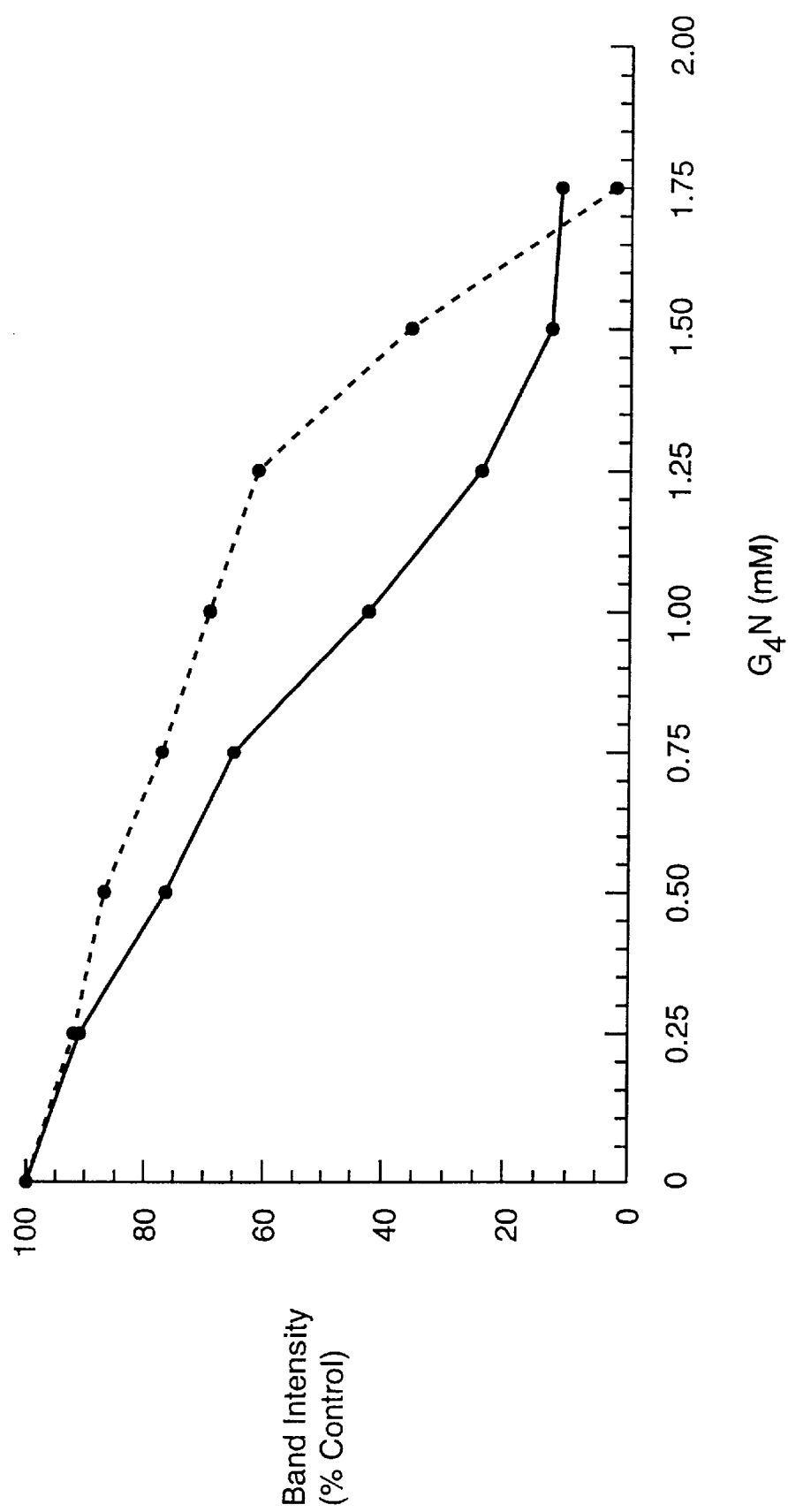

FIG. 13. Electrophoretic mobility shift assay (EMSA) of $G_4N$ interaction with the HIV Sp1-binding sites (−87 to −49). (A) $G_4N$ inhibition of Sp1-167D binding to ³²P labeled HIV Sp1 DNA template. Lane 1, template alone; lane 2, template plus 0.1 μg Sp1-167D; lanes 3–9, template incubated with increasing concentrations of $G_4N$ (0.25 to 1.75 mM) prior to the addition of 0.1 μg Sp1-167D. (B) $G_4N$ displacement of Sp1-167D bound to HIV template. Lane 1, template alone; lane 2, template plus 0.1 μg Sp1-167D plus 100-fold excess of unlabeled template; lane 3, template plus 0.1 μg Sp1-167D; lanes 4–10, Sp1/DNA complex challenged with increasing concentrations of $G_4N$ (0.25 to 1.75 mM); lane 11, template incubated in reaction buffer containing 1.75 mM $G_4N$. (C) Sp1-167D displacement of $G_4N$ bound to template. Lane 1, template alone; lanes 2–4, template plus increasing amounts of Sp1-167D (0.075, 0.150, 0.300 μg); lanes 5–8, template incubated in reaction buffer containing 1.2 mM $G_4N$ followed by challenge with increasing amounts of Sp1-167D (0.075, 0.150, 0.300 μg), lane 8 received no Sp1-167D. (D) Plot of diminishing Sp1-167D/DNA complex band intensities in response to increasing concentrations of $G_4N$ used in (A) - - - ● - - - and (B) - - - ● - - - . The gels used were 5% non-denaturing polyacrylamide with each lane receiving 5 μl of each reaction volume as described in experimental section and Ref. [1].

Figure 14:
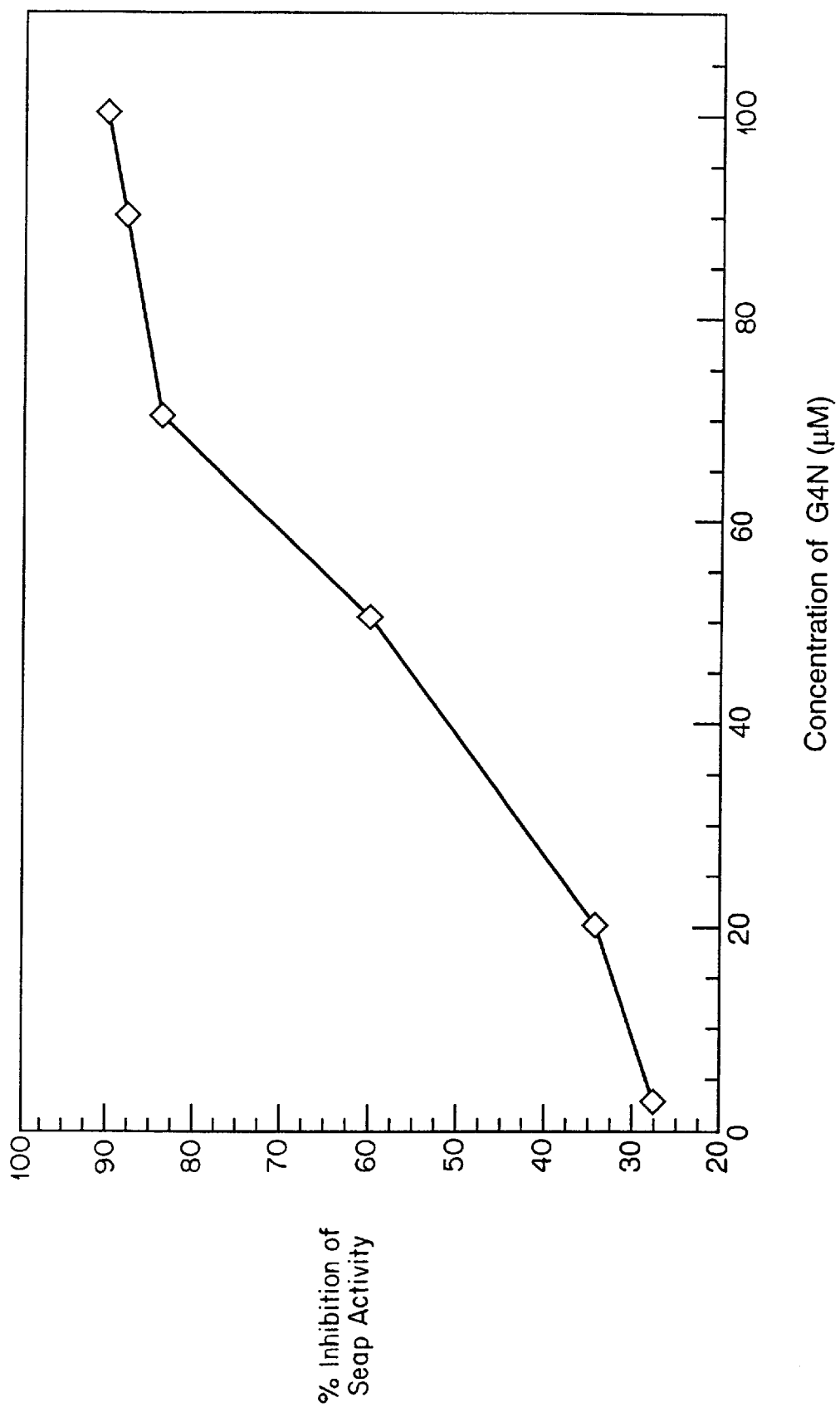

FIG. 14. Inhibition of HIV Tat-regulated transactivation in Cos cells by $G_4N$.

Figure 15:
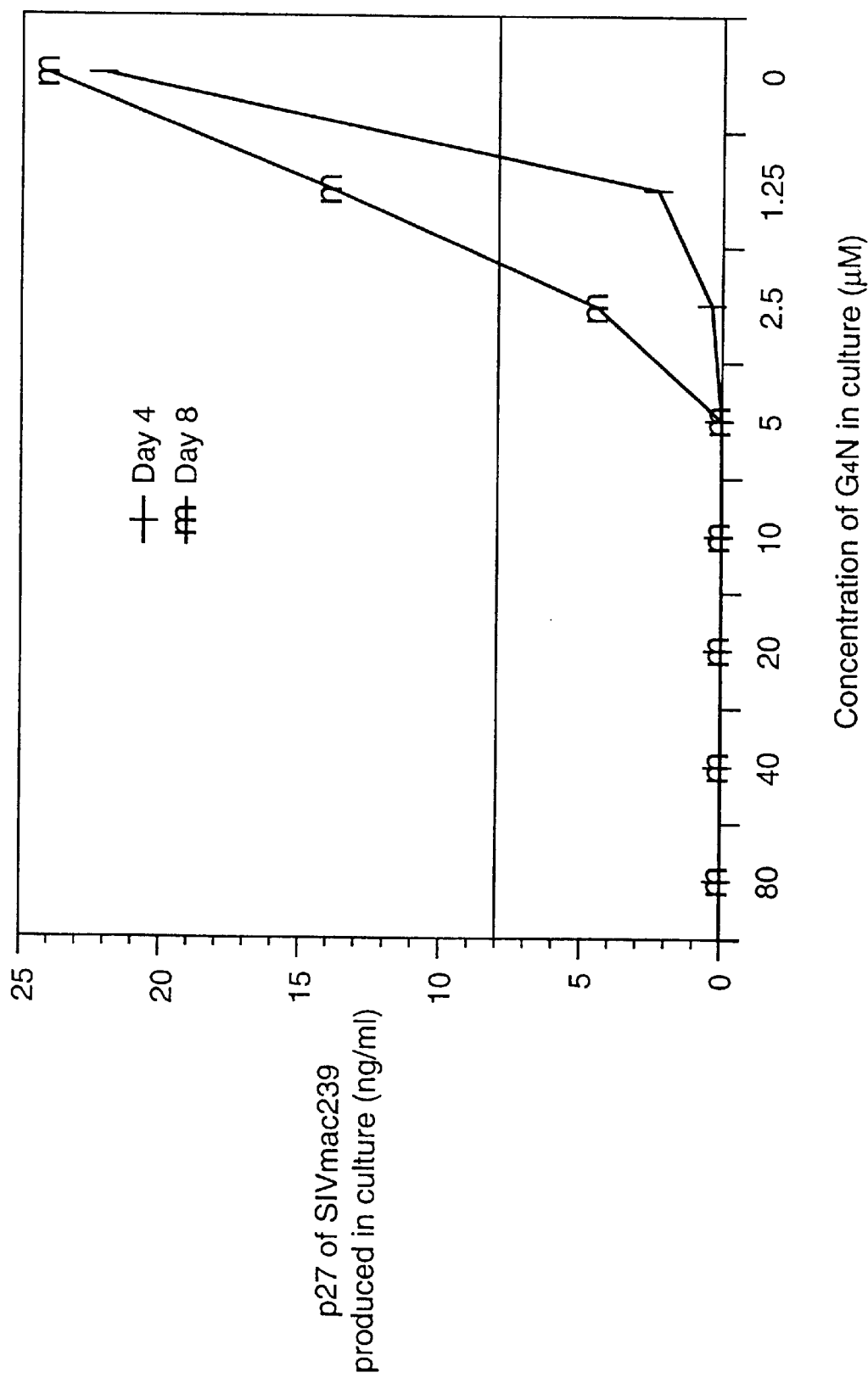

FIG. 15. SIV production with presence of $G_4N$. 107 174×cells were mixed with a 24 hrs. harvest stock of SIV mac 239 (4 ng of p27) for two hours at 37. Cells were resuspended and 1×105 cells in 100 μl medium were added to each well of three 96-well plates. Various concentrations of $G_4N$ from a freshly made stock were prepared and added to each of the six designed well. Culture supernatants were collected after four and eight days for viral production analysis. Viral production was assayed by a modified p27 capsid protein antigen capture ELISA as described in experimental section.

Figure 16:
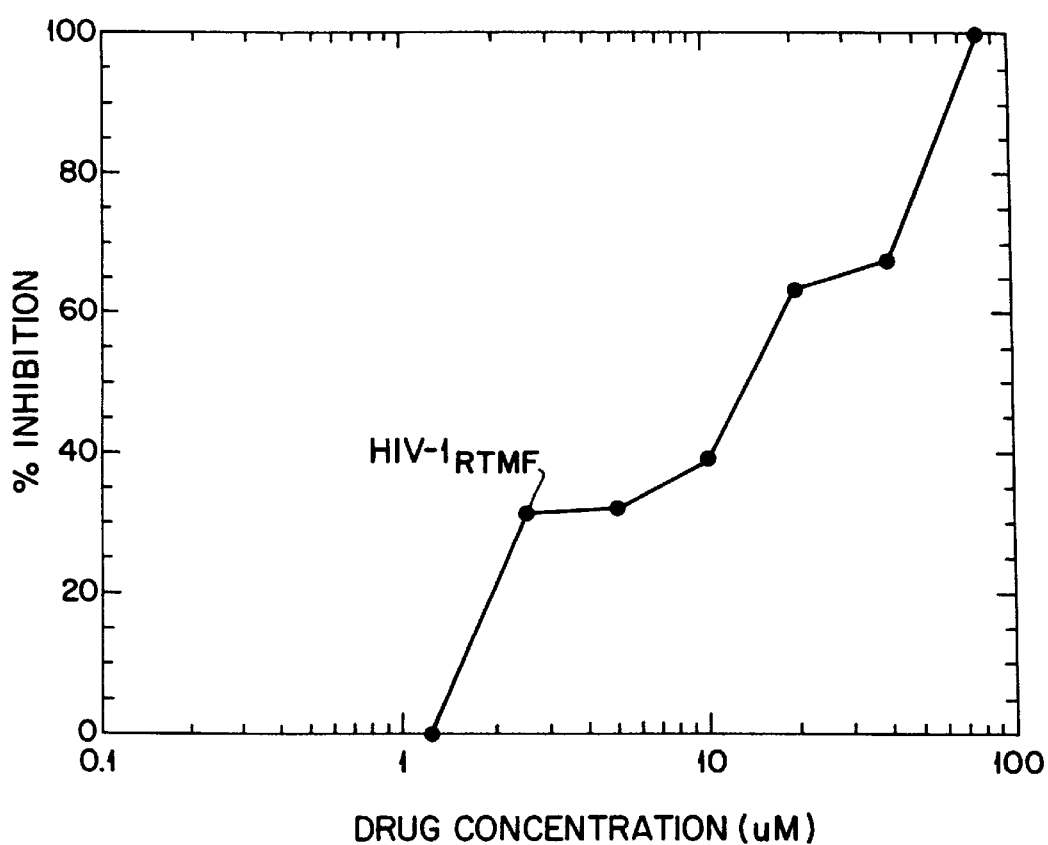

FIG. 16. Inhibition of HIV p24 antigen production in H9 cells by $G_4N$. Inhibition in percentage was calculated by comparing p24 level from an average of two duplicate cultures of $G_4N$ treated and not treated H9 cells 9 days following viral infection with a AZT resistant HIV strain, HIV-1RTMF.

DETAILED DESCRIPTION OF THE INVENTION

Experimental Methods

NDGA derivatives were synthesized chemically (15). Cell line C3 is a HPV16E+L plus activated Ras transformed cell line of C57 BL/6kh origin provided by W. Martin Kast of Loyola University Medical Center, Chicago, Ill., U.S.A. It is maintained and cultivated as described by Greenstone et al (21) and Feltkamp et al. (22, 23).

Synthesis of $G_4N$

Standard Procedure for the Preparation of meso-1,4-Bis[3,4-(dimethylaminoacetoxy)phenyl]-(2R,3S)-dimethylbutane Hydrochloride Salt Tetraglycinyl NDGA, $G_4N$. To a dichloromethane (250 ml) solution containing NDGA (12.8 g, 42.3 mmol, 1.0 equiv) and N,N,-dimethylglycine (26.2 g, 254 mmol, 6.0 equiv) were added DCC (52.4 g, 254 mmol, 6.0 equiv) and DMAP (2.32 g, 18.9 mmol, 1.0 equiv). The reaction mixture was stirred for 24 h under nitrogen at room temperature. After the reaction mixture was filtered, the solution was concentrated under reduced pressure. Acetone (250 ml) was then added into the reaction flask and the solution was bubbled with excess HCL(g). The water-soluble precipitate was dissolved in $H_2O$ and re-precipitated twice at room temperature from acetone to give (1) (29, 2 g, 36.8 mmol) as a white solid in 87% yield. Proton NMR spectra were obtained on a Varian Unity-400 (400 MHz) spectrometer by use of $D_2O$ solvent and TSP as internal standard. Carbon-13 NMR spectra were obtained on a Varian Unity-400 (400 Mhz) spectrometer by use of $D_2O$ as solvent. Carbon-13 chemical shifts are referenced to the TSP singlet (δ0.0 ppm).

The synthesis is depicted in Scheme 1.

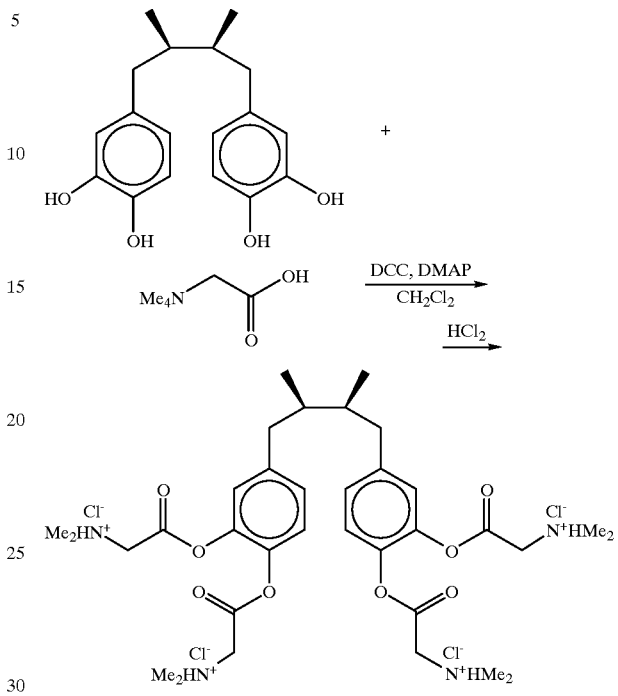

Scheme 1

General Procedure. All reactions were carried out in oven-dried glassware (120° C.) under an atmosphere of nitrogen, unless as indicated otherwise. Acetone, dichloromethane, 1,4-dioxane, ethyl acetate, hexanes, and tetrahydrofuran were purchased from Mallinckrodt Chemical Co. Acetone was dried with 4A molecular sieves and distilled. Dichloromethane, ethyl acetate, and hexanes were dried and distilled from $CaH_2$. 1,4-Dioxane and tetrahydrofuran were dried by distillation from sodium and benzophenone under an atmosphere of nitrogen. Nordihydroguaiaretic acid was purchased from Fluka Chemical Co. N,N'-Dicyclohexylcarbodiimide (DCC), 4-dimethylaminopyridine (DMAP), morpholine, triethylamine, and potassium carbonate were purchased from Merck Inc. 1-Bromo-3-chloropropane, N,N-dimethylglycine, and methyl phosphorodichloridate were purchased from Aldrich Chemical Co.

Analytical thin layer chromatography (TLC) was performed on precoated plates (silica gel 60 F-254), purchased from Merck Inc. Gas chromatographic analyses were performed on a Hewlett-Packard 5890 Series II instrument equipped with a 25-m cross-linked methyl silicone gum capillary column (0.32 mm i.d.). Nitrogen gas was used as a carrier gas and the flow rate was kept constant at 14.0 mL/min. The retention time $t_R$ was measured under the following conditions: injector temperature 260° C., isothermal column temperature 280° C. Gas chromatography and low resolution mass spectral analyses were performed on a Hewlett-Packard 5890 Series II instrument equipped with a Hewlett-Packard 5971A Mass Selective Detector and a capillary HP-1 column. Separations by medium-pressure liquid chromatography (MPLC) were performed at a flow rate of 120 mL/h by use of a Jasco Model 880-PU intelligent HPLC pump. The MPLC packing material, Reversed Phase Silica Gel C18 (particle size 0.035–0.070 mm), was purchased from Knauer Co. Purification by gravity column chromatography was carried out by use of Merek Reagents Silica Gel 60 (particle size 0.063–0.200 mm, 70–230 mesh ASTM).

Infrared (JR) spectra were measured on a Bomem Michelson Series FT-IR spectrometer. The wave numbers reported are referenced to the polystyrene 1601 cm~1 absorption. Absorption intensities are recorded by the following abbreviations: s, strong; m, medium; w, weak. Proton NMR spectra were obtained on a Varian Unity-400 (400 MHz) spectrometer by use of $D_2O$ as solvent and 3-(trimethylsilyl)propionic acid, sodium salt as internal standard. Carbon-13 NMR spectra were obtained on a Varian Unity-400 (100 MHz) spectrometer by used of $D_2O$ as solvent. Carbon-13 chemical shifts are referenced to the center of the 3-(trimethylsilyl)propionic acid, sodium salt singlet (60.0 ppm). Multiplicities are recorded by the following abbreviations: s, singlet; d, doublet; t, triplet; q, quartet; m, multiplet; J. coupling constant (hertz). High-resolution mass spectra were obtained by means of a JEOL JMS-HX100 mass spectrometer.

meso~1,4Bis[3,4(dimethyleminoacetoxy)phenyl]-2R,3S-dimethylbutane Hydrochloride Salt (2). To a solution of NDGA (1, 12.81 g, 42.37 mmol, 1.0 equiv) and N,N-dimethylglycine (26.21 g, 254.2 mmol, 6.0 equiv) in dichloromethane (250 mL) was added DCC (52.45 g, 254.2 mmol, 6.0 equiv) and DMAP (5.176 g, 42.37 mmol, 1.0 equiv). The reaction mixture was stirred for 24 h under nitrogen at room temperature. After dicyclohexylurea in the reaction mixture was filtered off, the resultant solution was concentrated under reduced pressure. Acetone (250 mL) was then added into the residue and the resultant solution was bubbled with excess HCl (g). The precipitate was dissolved in water and re-precipitated twice by use of acetone at room temperature to give 2 (28.97 g, 36.86 mmol) as a white solid in 87% yield: $^1$H NMR ($D_2O$, 400 MHz) δ 0.78 (d, J=6.0 Hz, 6 H. 2×$CH_3$), 1.73 (m, 2H. 2×CH), 2.38 (dd, J=13.2, 9.6 Hz, 2H. 2×ArCH), 2.78 (dd, J=13.2, 4.4 Hz, 2 H. 2×ArCH), 3.03 (s, 24 H. 8×$CH_3$N), 4.53 (s, 8H, 4×$CH_2$N), 7.22 (m, 4H. 4×ArH), 7.29 (d, J=8.4 Hz, 2H. 2×ArH); $^{13}$C NMR($D_2O$, 100 MHz) δ 18.11, 40.82, 41.73, 46.75, 59.59, 125.79, 126.58, 131.63, 140.66, 142.47, 146.11, 167.84; IR (KBr) 3461 (br), 2963 (m), 1777 (s, C=O), 1620 (m), 1478 (m), 1377 (m), 1210 (m), 1106 (m), 961 (w), 852 (w) cm$^{-1}$; MS (FAB) of (2–4 HCl) m/z (relative intensity) 643 (M+, 30), 600 (20),558 (43),515 (20), 473 (42), 430 (13), 388 (26), 185 (18), 93 (38),58 (100), 44 (22); HRMS (FAB) of (2–4 HCl) calcd for $C_{34}H_{50}N_4O_8$ 642.3628, found 642.3614; Anal. Calcd for $C_{34}H_{54}N_4O_8Cl_4$: C, 51.78; H. 6.90; N. 7.10; O. 16.23. Found: C, 51.70; H. 6.85; N. 7.05; O. 16.21.

It will be appreciated that by suitable substitution of other N,N-dimethyl-substituted amino acids, additional amino acid substituted compounds of the invention can be synthesized.

EXAMPLE 1

Effect of $M_4N$ and Several other NDGA Derivatives of SP1-regulated HPV $E_6/E_7$ Promoter Activity The effect of $M_4N$ and several other NDGA derivatives of SP1-regulated HPV $E6/E_7$ promoter activity was examined using luciferase as a reporter. The assay depends upon DNA transfection of the HPV16 LCR ($P_{97}$ promoter) fused to the luciferase reporter gene into C33A cells by calcium phosphate methods. C33A is a cervical tumor cell line (ATCC accession no. HTB-31) that does not contain any integrated HPV DNA, but has transcription factors necessary for a robust expression of the HPV early gene promoter. One day following DNA transfection various drug concentrations dissolved with the help of dimethyl sulfoxide (DMSO) were added to the cells. Thirty hours after drug treatment (so that the assay is complete within the standard forty-eight hours for transient transfection experiments), the cells were lysed and specific luciferase activity was determined (Luciferase Assay Systems, Promega, U.S. Pat. No. 5,283,179). As the $M_4N$ drug concentration was increased the specific luciferase activity decreased.

The results (shown in FIG. 2) demonstrate that $M_4N$ dramatically reduces Sp1 regulated transcription initiation at the HPV $E_6/E_7$ promoter in luciferase assay.

EXAMPLE 2

Inhibition of $E_6/E_7$ mRNA Synthesis Following $M_4N$ Treatment

Figure 3A:
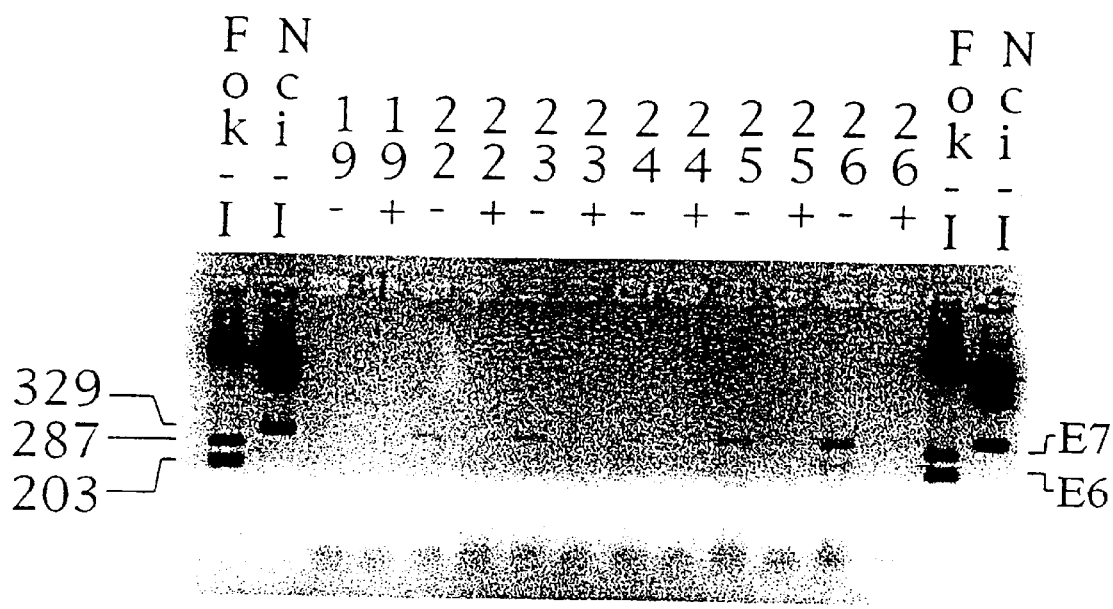
FIGS. 3A–3C. Inhibition of Viral $E_6$ and $E_7$ RNA Transcripts by 40μM $M_4N$. Total RNA isolated from C3 cells treated with either 40 μM $M_4N$ or DMSO alone in growth media for 71 hours was subjected to relative RTPCR. The RTPCR samples were removed after increasing cycles of amplification and resolved on an agarose gel. The gel photographs (3A and 3B) indicate these cycles, the presence of (+) or absence (−) of $M_4N$ in the growth media, and two digests of a pGMT vector used as size markers. The amplification map (2C) indicates the two expected size products of the amplification, resulting from the alternate splicing of the early viral RNA transcript.
Figure 3B:
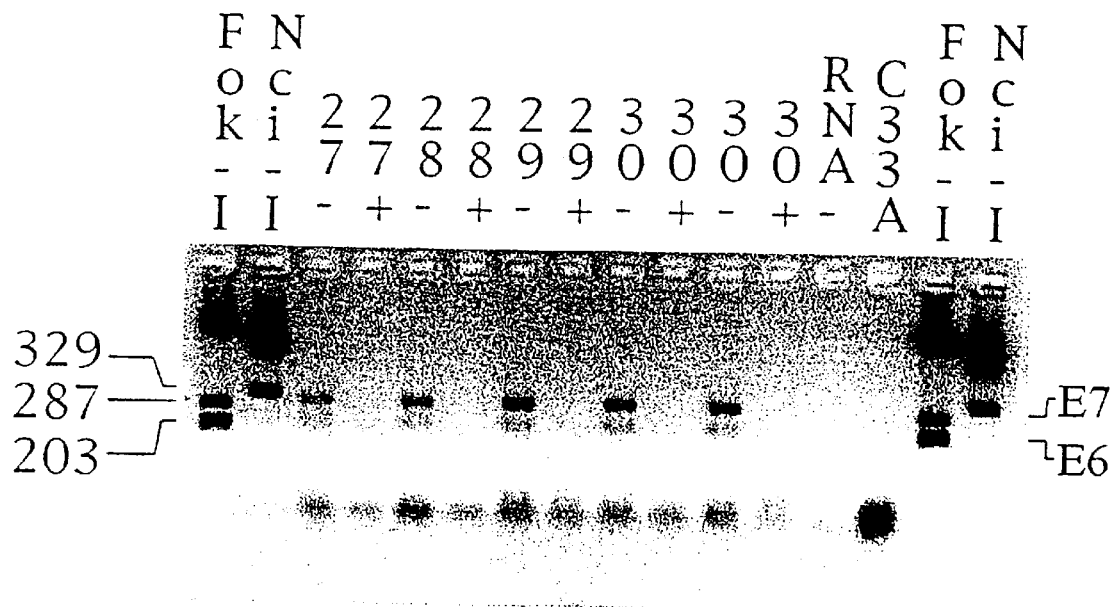
Figure 3C:
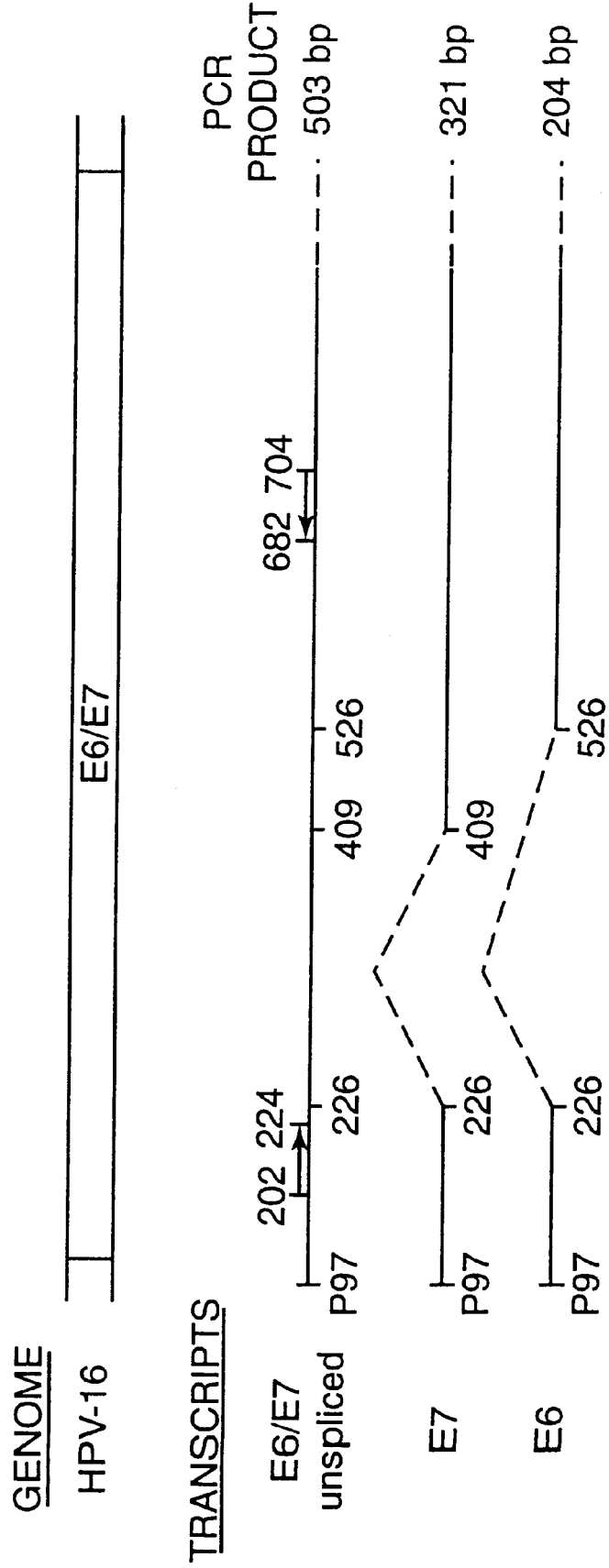

Inhibition of $E_6/E_7$ mRNA synthesis following $M_4N$ treatment was measured by RT-PCR in cervical cell line $C_3$. Relative RT-PCR was performed with quantities of total cellular RNA standardized to the cell numbers counted. The RT-PCR product was analyzed on a 2% agarose gel. The results are shown in FIG. 3. The RT-PCR results indicated that the amplified cDNAs of the expected size for E7 (321 bp) and E6 (204 bp) were detected in the DMSO treated cells as early as cycle 22 of amplification. These same products were barely detectable in the drug treated RNA extracts following 30 cycles of amplification. No amplified products were detected for the no template PCR control or from total RNA extracts of the HPV16-negative C33a cell line.

EXAMPLE 3

Inhibition of Cervical C3 Cell Growth by $M_4N$ Treatment

Figure 4A:
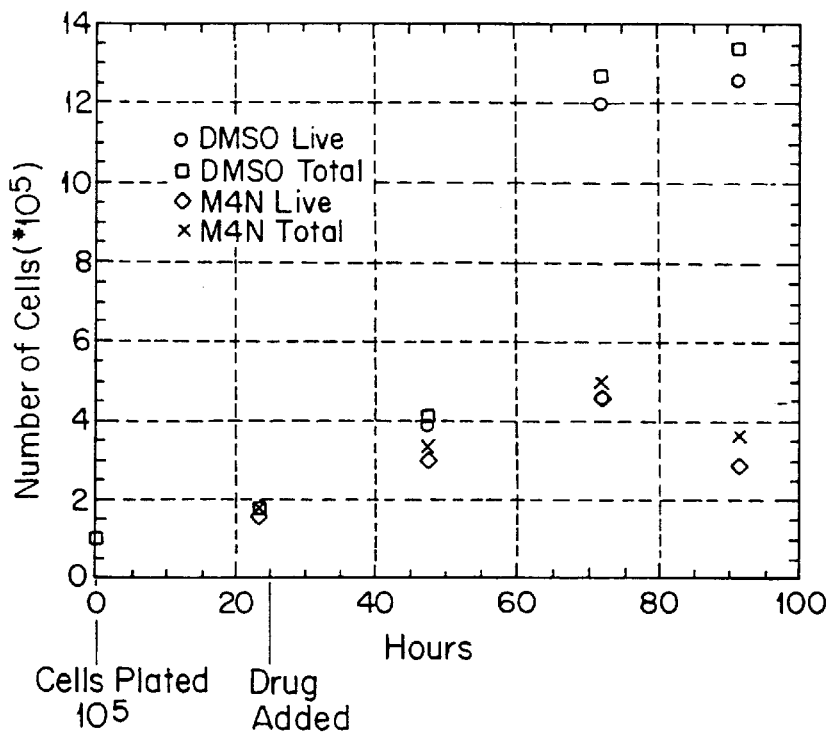
FIG. 4A. Inhibition of C3 Cell Growth by $M_4N$

HPV-16 transformed immortal mouse epithelial cells (C3 cells) were plated at a density of $10^5$ cells per vial. After 24 hours, ½ of the vials were given growth media containing 40 $\mu$M$M_4$N dissolved in 1% DMSO while the other half were given growth media containing only 1% DMSO. The results are shown in FIG. 4A. Within 24 hrs a difference in cell morphology between drug treated and control C3 cells was observed. The growth and division of the drug treated cells was markedly reduced in comparison to the untreated control, while the fraction of viable cells compared to the total cell count remained constant for both drug treated and DMSO only control cells. This indicates that $M_4N$ dramatically reduces cell division.

Figure 4B:
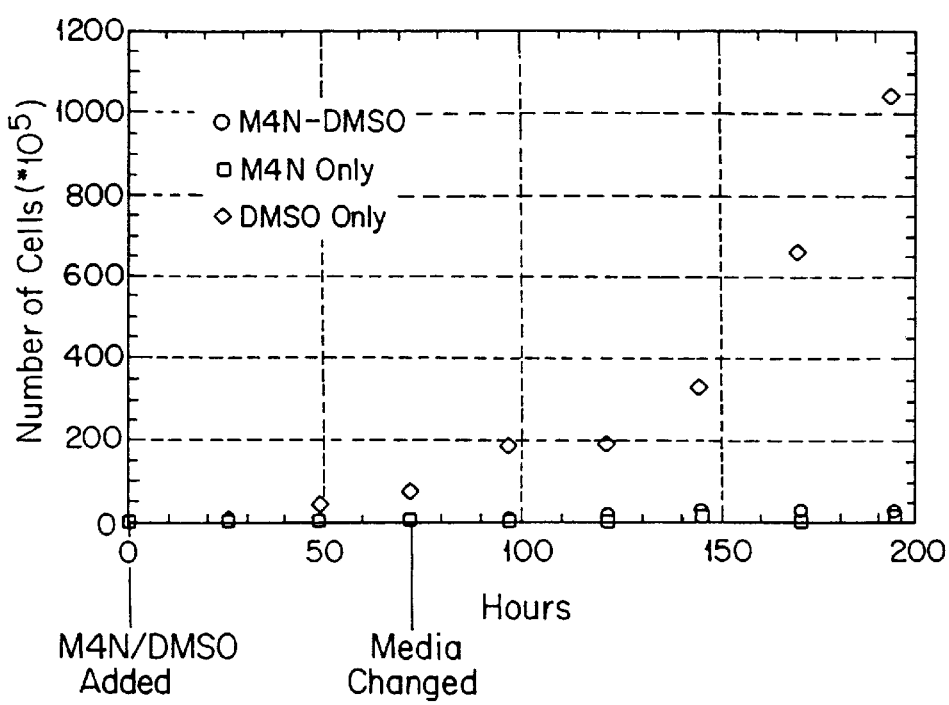
FIG. 4B. Inhibition of C3 Cell Growth Following the Removal of $M_4N$

The effect on C3 growth following removal of $M_4N$ from the medium was also examined. C3 cells were plated at a density of $10^4$ cells per vial. At time=0, ⅔ of the vials were given growth media supplemented with 40 $\mu$M $M_4N$ in 1% DMSO. The remaining vials were given growth media containing only 1% DMSO. After 73 hours, ½ of the vials that had received $M_4N$ in their growth media were washed and media containing only 1% DMSO was added. The other ⅔ of the cell vials were washed and replaced with the same media administered before. The results, shown in FIG. 4B, indicate that the rate of cell growth was not notably increased in $M_4N$ treated sample following the change to drug-free media, indicating that $M_4N$ continues to significantly reduce cell division even after its removal from the extracellular environment.

EXAMPLE 4

Analysis of Cellular Gene Expression in C3 Cells Before and After 72 hrs of Drug Treatment Gene expression with 9600 gene arrays was studied (FIG. 5). Five micrograms each of poly A$^+$ RNA from 72 hrs. $M_4N$ (40 μm) treated (C3 M$_4$N) and non-treated (C$_3$ DMSO) was used in a pair of human 9600 gene array hybridization study according to the procedure described in Genomics 51, 313–324 1998. The hybridization image was captured by a color video camera with a Nikon 55 mm AF micro Niko lens and digitized by a Macintosh LC630 computer. Such detection via enzyme substrate reaction of color-forming enzymes in either single or dual-color mode is reproducible and extremely sensitive (can detect <5 copies of transcript per cell with RNAs from $10^7$ cells).

The computer print outs showing differentially expressed genes (C$_3$ M$_4$N/C$_3$ DMSO>10 and C$_3$ DMSO/C$_3$ M$_4$N>10) were listed for examination. Image files in TIFF format and data files in MS excel format are kept on ZIP diskette. Gene names and clone ID numbers are available for obtaining Image clones for future northern blot confirmation.

Among a group of genes that are either up-regulated or down-regulated 72 hrs after M$_4$N treatment, the following are those specifically related to cell division and apoptosis. Several other cell cycle related genes are also greatly upregulated in response to M$_4$N. In addition to cyclin-dependent kinase CDC2 (Example 11), for example:

|  | Increase |
|---|---|
| Cyclin-dependent kinase inhibitor | (100X) |
| Apoptosis (APO-1) antigen | (100X) |
| Death Domain Three DR$_3$ | (100X) |
| Ras-related protein RAP-1 | (60X) |
| Human Map Kinase | (40X) |

The following cell cycle related genes are greatly down-regulated in response to M$_4$N:

|  | Treated | Untreated |
|---|---|---|
| Cyclin-dependent kinase 7 | (5%) | 100% |
| Human cytokine receptor | (2%) | 100% |
| Proliferating cell nuclear antigen, PCNA | (1%) | 100% |
| Human TNF-related Apoptosis APO$_2$ | (3%) | 100% |
| Cysteine protease | (7%) | 100% |

At earlier time points, such as after one hour drug treatment, $E_6/E_7$ level was found to be similar with those in control cells while after 4.5 hrs, $E_6/E_7$ were no longer detectable by RT-PCR (39). Gene expressions with 9600 gene arrays can be repeated with RNA isolated from these short-time treated cells (1 hour and 5 hours) in order to further pin down the initial cellular effects of the drug.

EXAMPLE 5

Targeting C3 Tumor Growth in Mice by Local Injection of M$_4$N

Figure 7:
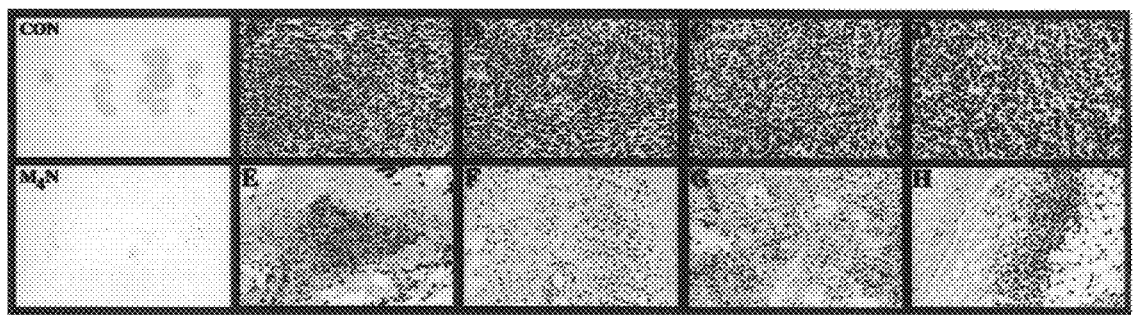
FIG. 7. Histopathology Effect of $M_4N$ and $M_4N/G_4N$ on Tumor Growth in Mice

Thirty six C57bl-16 NCR mice were injected with $5 \times 10^5$ C3 cells between the shoulders on the backs of the mice. Twenty four of the mice developed tumors within 20 days. Daily injection (50 μl–100 μl of M$_4$N or M$_4$N/G$_4$N) (200 mg/ml M$_4$N in DMSO, 200 mg/ml G$_4$N in PBS) showed profound effect in tumor growth in animals, as shown in Tables 1 and 2, FIGS. 6 and 7.

TABLE 1

M$_4$N and G$_4$N Effect on Growth of Single Tumors Developed in Mice

| Mouse # | Treatment Period Days 1–16 | | Lesion Size (mm) | | | Wt. Of Excised Lesion (g) | | Body wt. (g) | | |
|---|---|---|---|---|---|---|---|---|---|---|
| | | | Day 1 | Day 7 | Day 21 | Day 16 | Day 24 | Day 1 | Day 16 | Day 24 |
| 1 | DMSO* | | 3 × 8 × 3.3 | — | 5 × 7 × 4 | — | 0.3 | 18.8 | — | 20.2 |
| 2 | DMSO | | 4.4 × 6 × 3.5 | 10 × 12 × 8 | — | 1.56 | — | 19.6 | 20.5 | — |
| 3 | DMSO | | 0.8 × 0.8 × 1 | — | 10.5 × 11 × 9 | — | 1.14 | 18.2 | — | 16.1 |
| 4 | DMSO | | 2.8 × 3.8 × 2.5 | — | 18 × 11 × 9 | — | 2.9 | 17.6 | — | 20.2 |
| | Days 1–16 | | | | | | | | | |
| 6 | M$_4$N | | — | 9 × 8 × 5 | — | 0.2 | — | 19 | 19.2 | — |
| 7 | M$_4$N | | — | 6 × 7 × 7 | — | — | 0.1 | 18.2 | — | 20.4 |
| 11 | M$_4$N | | 1 × 1.3 × 1 | 9.5 × 10 × 9 | — | — | 0 | 19.5 | — | 20.2 |
| 14 | M$_4$N | | 3.8 × 3.8 × 3.5 | 8 × 9 × 6 | — | 0.4 | — | 17 | 17.6 | — |
| 15 | M$_4$N | | — | 5 × 4 × 4 | — | 0.1 | — | 18.9 | 20.0 | — |
| 16 | M$_4$N | | 2.8 × 2.8 × 2.8 | 9 × 6 × 4 | — | 0 | — | 17.2 | 17.6 | — |
| 17 | M$_4$N | | 2.3 × 2.3 × 2.3 | 6 × 6 × 4 | — | 0.2** | — | 17.3 | — | — |
| | Days 1–10 | Days 9–17 | | | | | | | | |
| 18 | M$_4$N | G$_4$N | 3 × 2.8 × 3 | 8 × 7 × 5 | — | — | 1.0** | 18.8 | — | 21.1 |
| 19 | M$_4$N | G$_4$N | — | 5 × 5 × 5 | — | 0.2 | — | 18.2 | 19.9 | — |
| 21 | M$_4$N | G$_4$N | 1.8 × 1.8 × 1.8 | 9 × 10 × 5 | — | 0.2 | — | 17.3 | 19.2 | — |
| 22 | M$_4$N | G$_4$N | — | 7 × 7 × 5 | — | — | 0 | 17.9 | — | 19.5 |
| 27 | M$_4$N | G$_4$N | 2.5 × 5 × 2.5 | 9 × 6 × 6 | — | — | 1.8*** | 20 | — | 20.7 |
| 28 | M$_4$N | G$_4$N | 2.8 × 2.3 × 2.8 | 5 × 5 × 4 | — | 0.17 | — | 18.1 | 19.8 | — |
| 29 | M$_4$N | G$_4$N | 2.8 × 2.5 × 2.8 | 5 × 6 × 4 | — | — | 0.2 | 18.8 | — | 9.6 |

*DMSO = Vehicle for Drug
**Taken on Day 15
***Lesion contained mostly necrotic cells as also found in lesions from mouse 6, 7, 11, 14, 15, 17, 19, 21, 28, 19 (FIG. 6,7). There were no lesions left in mouse #11 and #22 following drug treatments. Tumors found in control mouse #1, 2, 3, 4 contained growing cells (FIG. 2).

Experimental Procedures

36 C57bl-16NCR mice were injected with $5 \times 10^5$ C3 cells/mouse. Injections were 100 μL made subcutaneously between the shoulders on the backs of the mice. Cells were suspended in low-salt HBSS and suspension uniformity was maintained by gentle vortexing.

24 mice developed tumors. Their lesion sizes were measured by dial caliper. These mice were shaved, weight and treatment begun (Day 1). Four mice were sequestered as controls. Control mice received 50 μL DMSO injected intratumorally daily. Experimental mice (10) received 50 μL $M_4N$ dissolved in DMSO (200 mg/mL). An additional 10 mice received $M_4N$ treatments for 8 days followed by $G_4N$ treatments (50 μL, 200 mg/mL in PBS) daily for 8 days. Injections were made to several regions of tumor. Mice anesthetized with ether or metaphane prior to injection.

Day 13: All mice have raised skin but to very different degrees. The skin of one $M_4N$ treated mouse (#7) has split open through which the "dried-out tumor" fell out.

Day 14: Injection volume raised to 100 μL.

Day 15: One $M_4N$ treated mouse (#17) died due to overdose of anesthesia/handling. The skin at the lesion site of #17 cracked with the "dried-out tumor" showing. It was dissected, and lesion excised and weighed.

Day 16: Four more $M_4N$ treated mice (#6,14,15,16), three $M_4N/G_4N$ treated mice (#19,21,28) and one control mouse (#2) were euthanized, dissected and weighed. Remaining control mice (#1,3,4) were examined non-invasively and were carrying tumors.

Day 21: Tumor sizes from control mice were measured by dial caliper. Observation: The skin at the lesion sites of mouse #10 and #12 ($M_4N$ treated regions) cracked with the "dried-out tumor" showing.

TABLE 2

$M_4N$ and $G_4N$ Effect on Growth of Treated Lesions in Mice Carrying Multiple Tumors

| Mouse # | Treatment Period Days 1–16 | | Lesion Size (mm) Day 1 | Day 7 | Wt. Of Excised Lesion (g) Treated* | Not Treated** | Body wt. (g) Day 1 | Day 24 |
|---|---|---|---|---|---|---|---|---|
| 9 | $M_4N$ | | 1.3 × 5 × 0.75 | 7 × 9 × 8 | 0.25 | 0.6 | 20.2 | 17.9 |
| 10 | $M_4N$ | | 2.3 × 2.5 × 2.3 | 9.5 × 10 × 9 | 0.1 | 2.9 | 17.5 | 22.1 |
| 12 | $M_4N$ | | 2.5 × 2.5 × 2.5 | 8 × 9 × 6 | 0.11 | 1.82 | 17.8 | 20.0 |
| | Days 1–9 | Days 10–18 | | | | | | |
| 20 | $M_4N$ | $G_4N$ | 1.8 × 1.8 × 1.8 | 9 × 10 × 5 | 0.1 | 0.2 | 17 | 20.2 |
| 24 | $M_4N$ | $G_4N$ | — | 7 × 9 × 6 | 0 | 1.7 | 17.2 | 20.8 |
| 26 | $M_4N$ | $G_4N$ | 5 × 3.3 × 2.5 | 7 × 7 × 7 | 0.2 | 1.9 | 19.3 | 20.6 |

*Drug in DMSO was injected directly to the tumor regions
**From adjacent tumors deprived of drug

TABLE 3

Toxicity Studies of $G_4N$ in Mice

| | Group | # of Mice | Route | Treatment per day | Days of Injection | Mortality |
|---|---|---|---|---|---|---|
| 1 | 187.5 mg/kg | 3 | Subcutaneous | 2X | 6 | 0/3 |
| 2 | 375 mg/kg | 3 | Subcutaneous | 1X | 6 | 0/3 |
| 3 | 750 mg/kg | 4 | Subcutaneous | 1X | 6 | 1/4 |
| 4 | 375 mg/kg | 2 | IV | 2X | 6 | 0/2 |

C57BL-16NCR female mice from NCI were used in this experiment.

Tetraglycinal NDGA ($G_4N$) was freshly made everyday in PBS in concentrations of 75 mg/ml. Injections of 0.05 ml for group 1, 0.1 ml for groups 2 and 4, and 0.2 ml for group 3 per treatment were made for a period of 6 days. Experiments lasted seven days. Body weights were determined before and after six days of injection. No significant weight changes were observed during the experimental period.

All treated mice, controls (mouse numbers 1–4) and experimental mice (mouse numbers 6,7,9,10,11,12,14,15, 16,17 $M_4N$ numbers 18–22, 24, 26–29 $M_4N/G_4N$) exhibited swelling. Measurements of lesion sizes were made by dial caliper. Some mice experienced mild bleeding due to injection.

The treatment regimen and results were as follows:

Day 10: Mice weighed again. All mice exhibited growth up to two grams.

Day 12: No treatments made.

Day 24: Mouse #7 skin recovered completely. The experiment was terminated on this date. All remaining mice, $M_4N$ treated (#7,9,10,11,12) and $M_4N/G_4N$ treated (#18, 20,24,26,29) were euthanized, dissected, examined and weighed.

The effects of $M_4N$ and $M_4N/G_4N$ on C3 tumor growth in mice are summarized in Tables 1 and 2 and FIGS. 5 and 6. Table 1 shows the drug effect on C3 cell growth in mice carrying single tumors. The average weight of four excised tumors of the control group was 1.48 g while weights of lesions from $M_4N$ treated and $M_4N/G_4N$ treated were 0.142 and 0.51 g respectively. Drug treated lesions consisted mainly of dried out necrotic cells (FIG. 6). Tumors from the control group appeared homogenous and contained actively growing cells. Table 2 shows the drug effect on C3 tumor growth in mice carrying multiple tumors. In this study, drug was injected into one of the tumors. The average weight of untreated tumors was 1.77 g while that of $M_4N$ treated lesions was 0.15 g. Similar results were obtained following $M_4N/G_4N$ injection—the average weight of untreated tumors was 1.27 g, while that of the drug treated lesions was only 0.103 g.

The body weight changes of all mice during the entire experimental period appeared insignificant (Table 1 and 2).

EXAMPLE 6

Drug treated ($M_4N$) and DMSO vehicle-treated or untreated tumors (CON) from two groups of mice were prepared for histopathology examination. The excised tumors were immediately fixed and then stored in 4% formaldehyde in phosphate buffered saline. The fixed tissue was then dehydrated through a series of graded alcohols and xylene and embedded in paraffin. The paraffin tissue blocks were thin sectioned and stained for microscopy with hematoxylin and eosin. Histopathology studies showed that the control tumors were unaffected by DMSO treatment and continued to grow. They show the high nuclear/cytoplasmic ratio, pleomorphic nuclear changes, high mitotic figures, spindle like sarcoma shape, and infiltration into the surrounding tissue characteristic of cancer cells.

In contrast, those tumors receiving $M_4N$ treatment discontinued growth shortly after treatment began. They demonstrate significant necrosis and are no longer viable. There is a small amount of drug precipitate visible at higher magnification, and focal areas show chronic inflammation and fibrosis. This healing effect leads to the shedding of these deceased tumor cells from the area. The same results are seen with $M_4N/G_4N$ treatment as with the $M_4N$ treatment alone. However, since $G_4N$ is water-soluble, it can spread to a larger area of the tumor than $M_4N$. It is expected that $G_4N$ when used with $M_4N$ synergistically may be more effective in trating tumors of large sizes (i.e. greater than 2 $cm^3$).

EXAMPLE 7

Effect of $M_4N$ on HSV-1 Skin Infection in Guinea Pig

The drug $M_4N$ was also tested in inhibition of HSV-1 replication in skin infections in guinea pigs. Guinea pig skin was pinched with needles and HSV-1 suppression was applied topically to infect each pricked area. $M_4N$ was then applied to the pricked infected area following infection daily for 6 days.

Six areas of bared back skin of a guinea pig were punched sterilely with a 5=DIN needle. Two areas were infected with HSV-1 (HSV-C, culture supernatant, or isolated HSV in saline, HSV-SC). The other four areas were infected with HSV-SC. Fifteen minutes after infection, 30 $\mu$l of test compounds ($ABDS_1$, $ABDS_2$, ACV and $M_4N$ (4N) in 60 mg/ml of DMSO were applied to each punched infected region of an area, five times per day for six days. $ABDS_1$ and $ABDS_2$ were included as negative controls. The photograph in FIG. 8 was taken at day 6 and shows the extent of HSV-1 replication in the absence of drugs (HSV-C, HSV-SC), in the presence of ineffective drugs (HSV-$ABDS_1$, HSV-$ABDS_2$) and in the presence of effective drugs (HSV-$M_4N$ and HSV-ACV). It can be seen that six large confluent blisters were developed in areas treated by HSV-C, HSV-SC, HSV-$ABDS_1$, HSV-$ABDS_2$, while no blisters were observed in infected areas following $M_4N$ (4N) and ACV treatments.

Clearcut results that $M_4N$ can block HSV replication were obtained in this model system as shown by the disappearance of the skin lesions and by no shedding of the virus 4 days after the drug treatment. Initial animal studies also showed $M_4N$ to be non-toxic to mice at concentrations as high as 300 mg/kg when given intraperitoneally, and as high as 375 mg/kg when given either subcutaneously or by IV (Table 3) (6).

EXAMPLE 8

$M_4N$ for Clinical Treatment Using in Situ Injection

Administration of $M_4N$ directly into tumors as a drug delivery route provides several distinctive advantages. 1) $M_4N$ is a hydrophobic compound and is exceedingly soluble in DMSO (200 mg/ml). Therefore only a small volume of the drug solution is needed for injection in order to achieve effective dosage of the drug. In the mouse study described in Example 5, above, daily injection of 50 $\mu$l to 100 $\mu$l for several days was sufficient to completely stop tumor growth in mice. There have been several previous studies on the use of large dosages (30 ml IV per treatment) of DMSO for treating diseases (24). The results were not conclusive (25). However, since tens of millions of people have been safely tested with large amounts of DMSO worldwide in the past, it appears that DMSO should be safe as a vehicle for drug delivery when only small volume of it will be used (26). 2) By injection in situ, a majority of the drug residue remains insoluble and concentrated in the tumor areas, and does not enter the circulatory system, thus whole body toxicity is avoided. In addition, since enough drug remains within the tumor to suppress its growth, continued injection of drug is unnecessary after relatively few treatments. In the mouse study of Example 5, tumor cells continued to die even after discontinuation of $M_4N$ injections. Thus when drug is directly targeted, tumor size becomes the determining factor for the required amount of drug to be administered. The difference between whole body weights of a human vs. a mouse becomes irrelevant. In the mouse tumor studies, 20 mg/day for 10 days were more than sufficient to eliminate tumors. There should be no reason to use a higher dosage than this for treating a human tumor of comparable size (1–1.5 $cm^3$). This should reduce the risk considerably in human trials.

EXAMPLE 9

$M_4N$ Treatment of Cells Blocks Cellular Proliferation

Figure 9A:
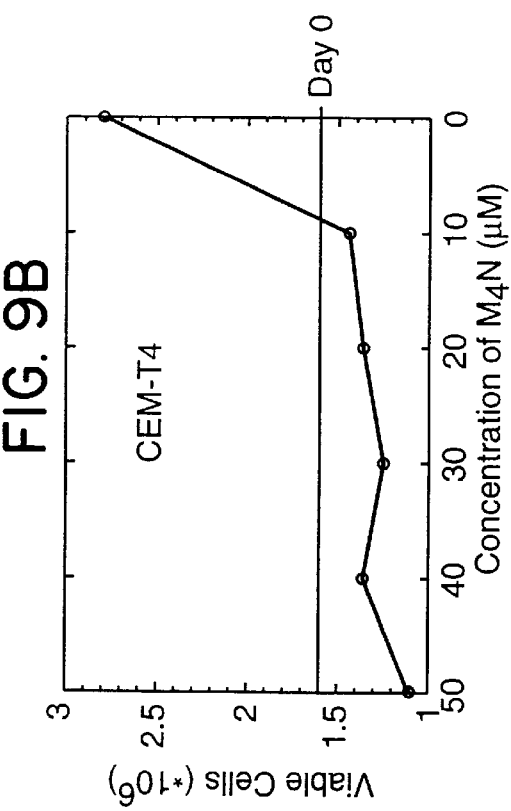
Figure 9B:
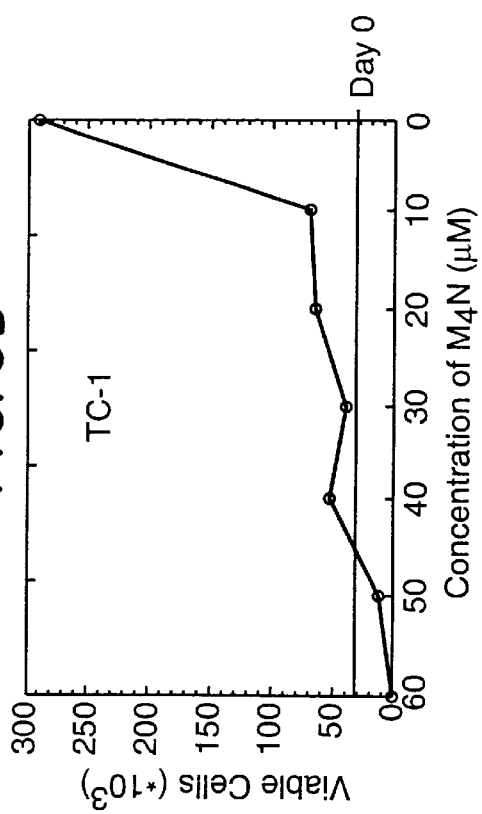
Figure 9C:
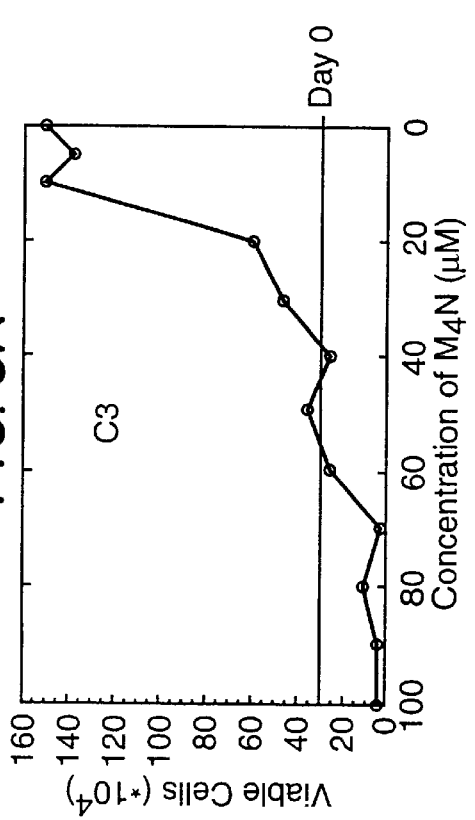

Our previous research on $M_4N$ indicated that it could inhibit viral transcription by deactivation of Sp1-dependent promoters. Many mammalian cell cycle genes also contain essential Sp1 promoters and $M_4N$ may therefore block their transcription. This hypothesis was tested by examining the antiproliferative effect of $M_4N$ on a number of different cell lines. Low concentrations (10 $\mu$M) of the parent compound, NDGA, have previously been shown to induce apoptosis in mammalian cells (27). This effect, however, can be circumvented by blocking one of the catechol oxygens or the addition of a hydrophilic group to NDGA (28). Increasing amounts of the NDGA derivative $M_4N$ were tested on cultures of the HPV-16/ras transformed C3 cell line (29) to determine the optimal concentration required to inhibit proliferation (FIG. 9a). The cells respond well to $M_4N$, ceasing division after 72 hours over the range of concentration from 40 to 60 $\mu$M. After three days at these concentrations the number of cells remained equal to the count at the initiation of treatment (day 0, FIG. 9). A more modest reduction in cell growth was observed at lower concentrations of the drug and some cell death was seen at concentrations greater than 60 $\mu$M.

Figure 9D:
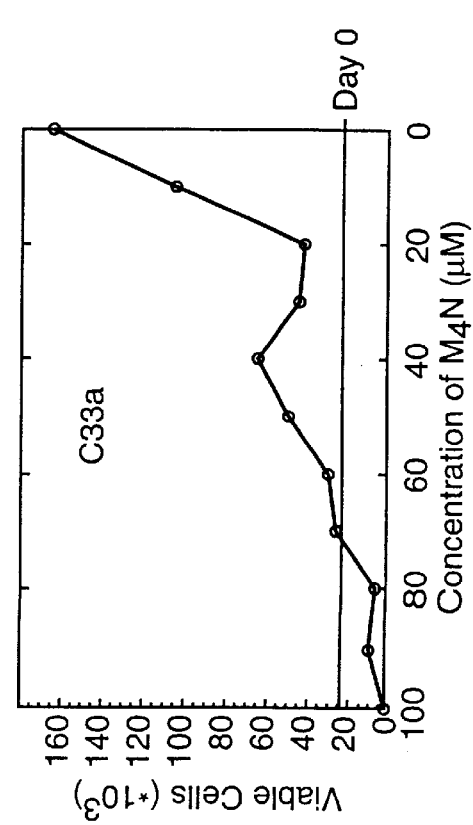
Figure 9E:
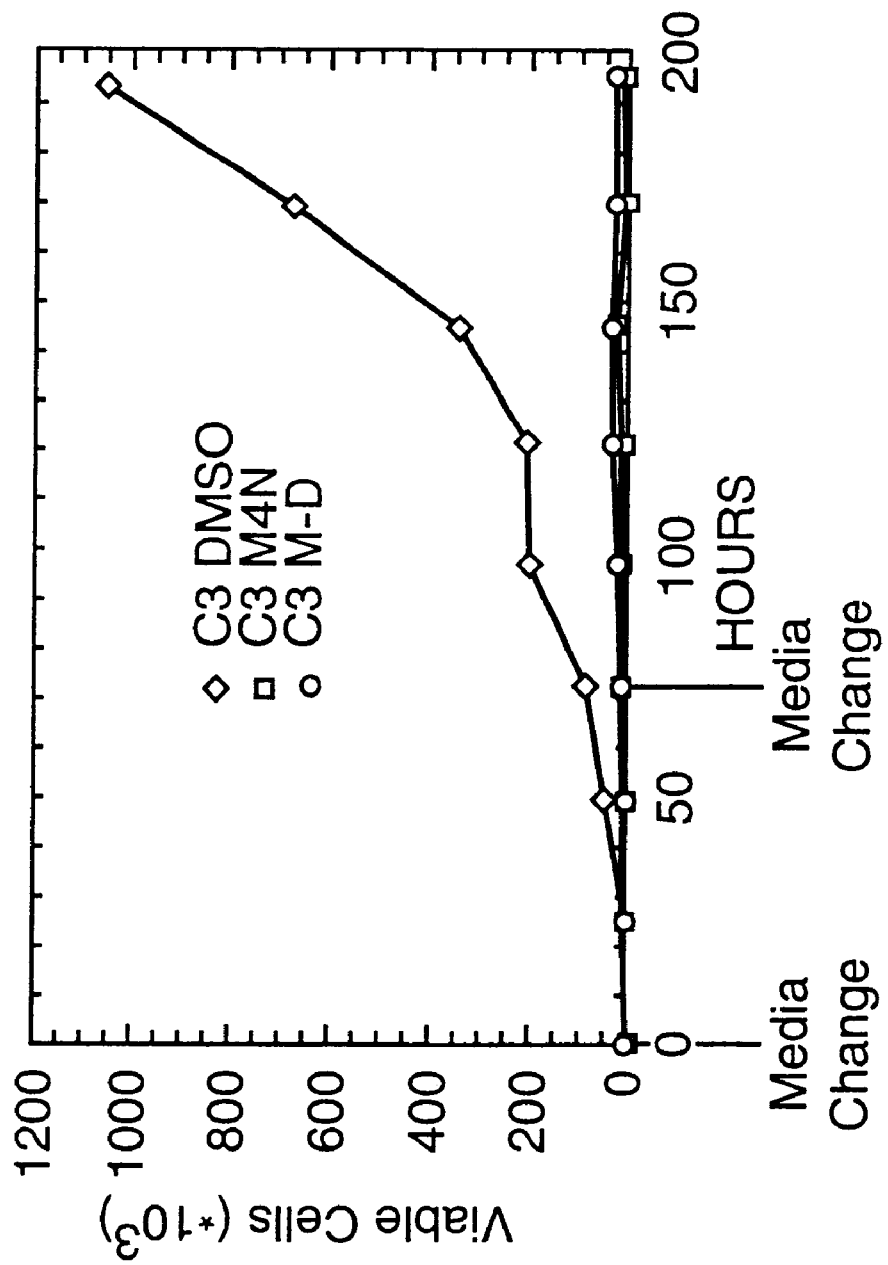

The antiproliferative effect of $M_4N$ on the C3 cell line is not solely due to the drug's ability to deactivate the Sp1-dependent HPV-16 E6/E7 oncogene promoter, as similar growth inhibition was observed in the HPV-16 transformed TC-1 cell line whose E6/E7 oncogenes are under control of a non-Sp1 dependent retroviral promoter (30) (FIG. 9d). In addition, growth of the C33a cell line (FIG. 9c), an HPV-negative human cervical cancer cell line, and the CEM-T4 line (FIG. 9b), a human leukemia cell line (31), was also blocked by treatment with $M_4N$. In the four cell lines that were treated with the drug, nearly all (>95%) of the arrested cells were viable until the concentration of $M_4N$ exceeded a "threshold" value (60 μM for C3 cells, 40 μM for TC-1 cells, etc.). Above these concentrations the percentage of viable cells decreases precipitously. Interestingly, arrested cells maintained >95% viability even after prolonged exposure to the drug. The C3 cells exhibited no increase in cell death after eight days of treatment with 40 μM $M_4N$ (FIG. 9e).

EXAMPLE 10

Cells Treated With $M_4N$ Arrest in G2 Phase

Once it was established that cells treated with $M_4N$ cease proliferation yet remain viable, analysis of cellular DNA content and fluorescence examination of cell structures were used to determine the point in the cell cycle where the cells arrest. Cells exposed to $M_4N$ for 72 hours demonstrated increased G2/M DNA content relative to the controls (FIGS. 10a–d). The most extreme responses were seen from the C3 and CEMT4 cell lines, in which >90% of the cells show G2/M DNA content.

In order to distinguish between an arrest in G2 or a mitotic block, antibodies against α tubulin (green) and γ tubulin (red) were used to determine the status of the centrosomes in the C3 cell line following 72 hours $M_4N$ treatment. As shown in FIG. 11a, the centrosomes of $M_4N$ treated cells are duplicated but still located next to each other in the nucleus of the cell. Since centrosomes separate during early prophase, it can be concluded that these cells have not begun mitosis. In contrast, the gamma tubulin staining of the control cells has the diffuse pattern characteristic of G1 or S phase (32). A lack of chromatin condensation in the $M_4N$ treated cells was also observed with DAPI staining (FIG. 12b), additional evidence that the cells have not moved forward out of G2 phase (33).

EXAMPLE 11

Production of CDC2 is Inhibited by 40 μM $M_4N$

Figure 12A:
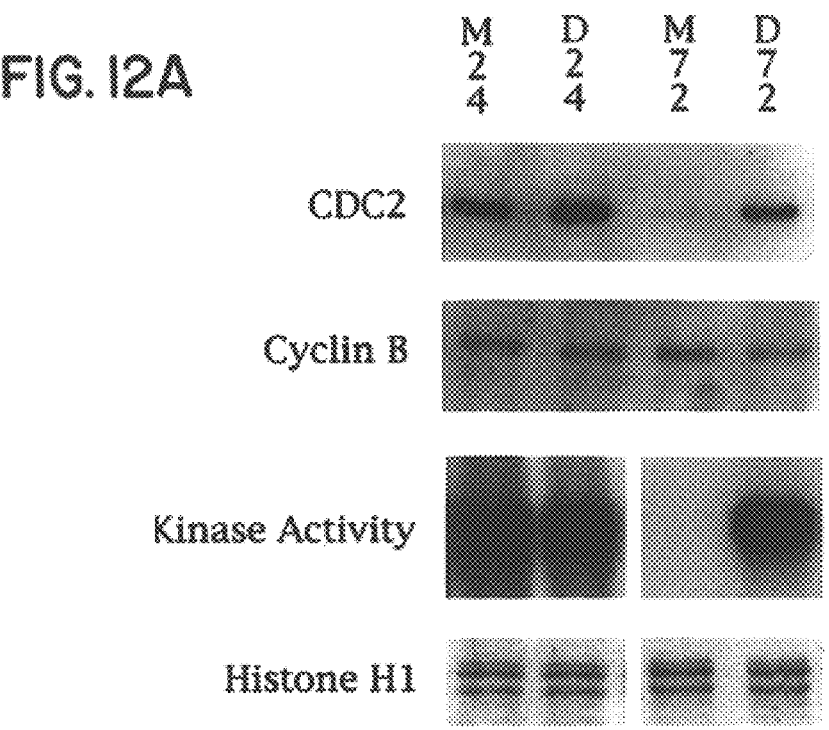

Since progression of cells out of G2 is dependent on the production of the MPF, the status of its protein components was examined in C3 cells treated with 40 μM $M_4N$. Asynchronous cells were grown for 24 or 72 hours in media containing either $M_4N$ in 1% DMSO, or 1% DMSO alone. The cells were harvested, and equal amounts of total cellular protein were analyzed by western blotting. A marked reduction in the amount of CDC2 was observed after 72 hours treatment with $M_4N$ (FIG. 12a). However, levels of cyclin B, detected by stripping and reprobing the same membrane, were found to be unchanged. These results indicate that, under these conditions, the arrest is not likely a response to p53 since it has been shown that overexpression of p53 leads to a decrease in cyclin B (34,35). Consistent with the results of the western analysis, CDC2 kinase activity was eliminated by 72 hours of $M_4N$ treatment (FIG. 12a). These experiments support the view that the drug acts by inhibiting the production of the CDC2 protein, resulting in a loss of activity of the MPF.

Figure 12B:
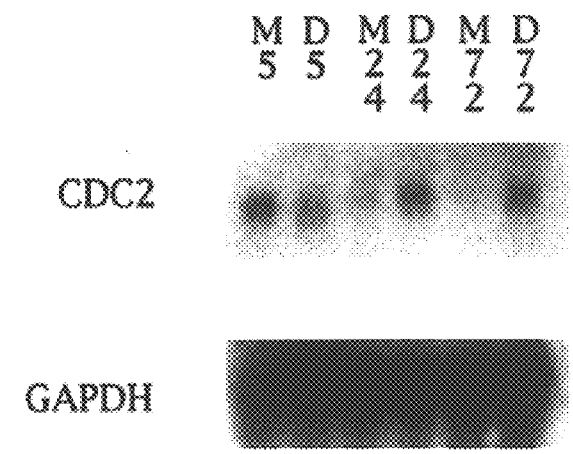

Our previous studies demonstrating the ability of $M_4N$ to block Sp1-dependent viral transcription suggest reduction of CDC2 mRNA levels as a possible mechanism for the decrease of CDC2 protein. This is consistent with the finding that the cyclin B protein, whose gene does not require Sp1 for its expression, is produced at normal levels while the CDC2 protein, whose gene has two essential Sp1 sites in its promoter, is substantially reduced in quantity. To test this hypothesis, northern blot analysis was performed on RNA harvested from C3 cells treated with 40 μM $M_4N$ for 5 to 72 hours. As shown in FIG. 12b, the amount of CDC2 mRNA is reduced after only 24 hours treatment with $M_4N$ and nearly eliminated after 72 hours. Production of the non-Sp1 regulated housekeeping gene GAPDH was used as an RNA loading control, and its levels were not effected by 40 μM $M_4N$.

Figure 12C:
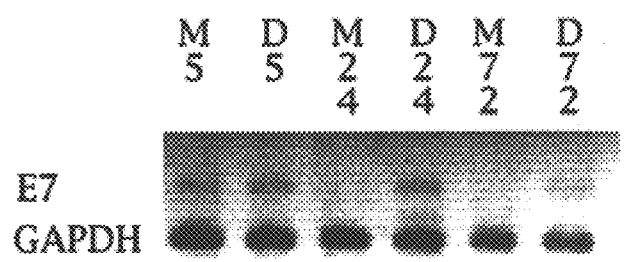

The use of the C3 cell line allows us an additional control for analysis of the mechanism of $M_4N$ mediated cell cycle arrest since other Sp1-dependent gene promoters are also likely to be inhibited by $M_4N$ treatment. This possibility was examined in C3 cells by analyzing the effect of $M_4N$ on transcription from the Sp1 dependent HPV-16 E6/E7 promoter. rtPCR analysis of RNA isolated from C3 cells treated with 40 μM $M_4N$ for 5 to 72 hours demonstrated a clear reduction in the levels of the E7 transcript (FIG. 12c). GAPDH was again used as an internal control in this experiment, and its levels were unaffected by drug treatment. These results provide additional evidence that $M_4N$ reduces the transcripts of Sp1 regulated promoters.

EXAMPLE 12

Inhibition of Sp1-Binding Activity by $G_4N$ in a Gel Mobility-Shift Analysis

Sp1 family proteins induce bends toward the major groove of DNA upon binding (36). The zinc finger domain of the Sp1 protein is responsible for the binding of the GC Box sequence 5'-GGGGCGGGG-3'. From computational analysis, it was determined that $G_4N$, the aminoester derivative of NDGA, could form a stable complex with such a sequence in the major groove. To determine whether $G_4N$ can serve as a Sp1 blocker as well as a Sp1 displacer, we performed Sp1/enhancer interaction studies in the presence or absence of $G_4N$ by the gel mobility-shift analysis using only the DNA binding domain of Sp1 for testing. In the blocking experiment, different concentrations of $G_4N$ were first incubated with $^{32}$P-labelled DNA in the binding buffer for 30 min at 25° C. DNA binding domain of recombinant Sp1 protein (Sp1-167D) was next added and incubated for additional 30 min in the presence of a large excess of BSA protein. In the displacement study, the recombinant SP1-167D was first allowed to bind DNA, $G_4N$ was then added at the second step of the incubation. The $G_4N$ and Sp1-167D concentrations and, the incubation and gel electrophoresis conditions were identical in both studies (experimental section). As shown in FIG. 13, in either case, $G_4N$ was found to be able keep DNA from interacting with Sp1-167D protein. When only the DNA binding domain of Sp1 alone was tested, $G_4N$ appeared to be more efficient in displacement of the bound Sp1 than blocking Sp1 from binding to the enhancer, as shown by the gel mobility-shift analysis (FIG. 13, A,B,D). We have also examined whether the bound $G_4N$ can be replaced by Sp1-167D. In this study, the inhibition of Sp1-167D binding by $G_4N$ was first established by the mobility-shift analysis (FIG. 13C lanes 2 and 5). When the $G_4N$ bound template was challenged with additional Sp1-167D, we observed a dosage dependent increase of the band intensities of the Sp1-167D/DNA complex (FIG. 6C, Lanes 6,7) indicating the displacement of $G_4N$ by Sp1-167D from the template.

EXAMPLE 13

Inhibition of Sp1 Regulated Tat-Transactivation of HIV Promoter Activity by G4N. As reported previously, methylated NDGA derivatives can block Sp1 binding to the enhancer sites of a variety of viral promoters including HIV, ICP4 of HSV, E6/E7 gene of HPV (37,38,39). We further tested the $G_4N$ effect on the Tat-transactivation of HIV promoter activity in Cos cells by the SEAP assay as previously described. Basal level of the HIV LTR driven SEAP expression was previously found to be barely detectable in Cos cells. There were 60-fold or more increase in SEAP expression when Cos cells were cotransfected with the CMV promoter driven Tat gene (37). Such Tat-driven transactivation of the HIV LTR promoter activity was previously shown to be Sp1 regulated (37,40). In the presence of G4N, we observed inhibition of HIV transactivation in a dose-dependent fashion (FIG. 14). An average value IC50 value of 36 $\mu$M for $G_4N$ was comparable to that of 3-O-methyl NDGA, Mal.4 ($IC_{50}$ 25 $\mu$M) and somewhat higher than that of tetra-methyl NDGA, $M_4N$ ($IC_{50}$ 11 $\mu$M). The differences perhaps are due to the chemical nature of the test compounds affecting the drug uptake to the cells.

EXAMPLE 14
Inhibition of SIV-1 and HIV-1 Production in Cell Cultures by G4N. Both HIV-1 and SIV are retroviruses that require integration into the host genome to complete their replication. Both rely on host transcription factors for their proviral transcriptions. Sp1 plays a central role for such expression in these two viruses sharing an almost identical mode of transcription regulation. In anticipation of using SIV infected rhesus monkeys as animal model for testing the antiviral effect of $G_4N$, we have studied and compared the $G_4N$ effect in inhibition of SIV in 174×CEM cells with that of HIV in H9 cells. Cellular toxicities of $G_4N$ in these two cell lines were also examined. For SIV inhibition study, 107 174×CEM cells were mixed with high titer stock of SIVmac 239 at 37° C. for two hours and then washed twice with cold PBS buffer to remove the unabsorbed virus. Cell suspension was aliquoted into each well of three 96 well plates. Various concentrations of the $G_4N$ solutions were made from freshly prepared stock and aliquoted separately and each to six wells in a column of one 96 well plate. Culture supernantants were collected every four days post infection, (P.I.) and fresh medium containing appropriate concentrations of the drug were added to the culture following supernatant collections. Viral production was assayed by a modified p27 core antigen capture ELISA as shown (FIG. 15). There was no SIV production detected using $G_4N$ in concentrations above 5 $\mu$M. At $G_4N$ concentrations below 2.5 $\mu$M, SIV production was detected (FIG. 15) in culture supernatants from 4th and 8th days post infected cultures as compared to viral production in the absence of the drug. $G_4N$ (250 $\mu$M or less) showed no toxic effect on uninfected 174×CEM cells, as determined by the MTT assay (41). A similar experiment was also carried out for the study of inhibition of HIV-1 by $G_4N$ in H9 cells. The H9 cells were subcultured at 1×105/ml and were infected with an AZT resistant strain of HIV-1 (HIV-1 RTMF). $G_4N$ in different concentrations was added two hours after infection. Fresh medium change was made every four days. Cell growth in the presence of $G_4N$ was monitored carefully during the nine-day experimental period. Viral production was assayed by a p24 core antigen capture ELISA. As shown (FIG. 16), $G_4N$ concentration of 80 $\mu$M completely inhibited HIV replication in H9 cells. An $IC_{50}$ of 12 $\mu$M $G_4N$ for the inhibition of HIV-1 RTMF was found. Again, there was no detectable toxicity to uninfected H9 cells within the range of the assay (and below 250 $\mu$M).

References cited herein are listed below for convenience and are hereby incorporated by reference.
1. Nurse, P., Universal Control Mechanism Regulating Onset of M-Phase. *Nature*, 344, 503–508.(1990.)
2. Fang, F. and J. W. Newport, Evidence That the G1-S and G2-M Transitions Are Controlled by Different cdc2 Proteins in Higher Eukaryotes. *Cell*, 66, 731–742.(1991.)
3. Dalton, S., Cell Cycle Regulation of the Human cdc2 Gene. *The EMBO Journal*, 11, 1797–1804.(1992.)
4. Morgan, D. O., Principles of CDK Regulation. *Nature*, 374, 131–134.(1995.)
5. Murray, A. W., Creative Blocks: Cell-cycle Checkpoints and Feedback Controls. *Nature*, 359, 599–604.(1992.)
6. Kao, G. D., M. W. G., and R. J. Muschel, p34(Cdc2) Kinase Activity Is Excluded From the Nucleus During the Radiation-induced G(2) Arrest in HeLa Cells. *J. Biol. Chem.*, 274, 34779–34784.(1999.)
7. Hwu, J. R., Tseng, W. N., Gnabre, J., Giza, P. and Huang, R. C. C. (1998) Antiviral Activities of Methylated Nordihydroguaiaretic Acids (I) Synthesis, Structure Identification and Inhibition of Tat Regulated HIV Transactivation. *J. Med. Chem.* 41:2994–3000.
8. Gnabre, J. N., et al., Inhibition of Human Immunodeficiency Virus Type 1 Transcription and Replication by DNA Sequence-Selective Plant Lignans. *Proc. Natl. Acad. Sci. USA*, 92, 11239–11243.(1995.)
9. Chen, H., et al., Antiviral Activities of Methylated Nordihydroguaiaretic Acids. 2. Targeting Herpes Simplex Virus Replication by the Mutation Insensitive Transcription Inhibitor Tetra-O-Methyl-NDGA. *Journal of Medicinal Chemistry*, 41,3001–3007.(1998.)
10. Craigol, J., et al., Inhibition of Human Papillomavirus Type 16 Gene Expression by Nordihydroguaiaretic Acid Plant Lignan Derivatives. *Antiviral Research*, 47, 19–28. (2000.)
11. Baba, M. (1997) Mini Review. Cellular Factors as Alternative Targets for inhibition of HIV-1. *Antiviral Res.* 33, 144 i–1452.
12. Gnabre, J. N., Brady, J. N., Clanton, D. J., Ito, Y., Dittmer, J., Bates, R. B. and Huang, R. C. (1995) Inhibition of Human Immunodeficiency Virus Type 1 Transcription and Replication by DNA Sequence-Selected Plant Lignans. *Proc. Natl. Acad. Sci. U.S.A.* 92, 11239.
13. Gnabre, J. N., Ito, Y., Ma. Y. and Huang, R. C. (1996) Isolation of Anti-HIV-1 Lignans from *Laffea Tridentata* by Counter-Current Chromatography. *J. Chromatogr.* A 719, 353.
14. Gnabre, J. N., Huang, R. C., Bates, R. B., Burns, J. J., Calder, S., Malcomson, M. E. and McClure, K. J. (1995) Characterization of Anti-HIV Lignans from *Larrea Tridentata Tetrahedron* 51, 12203.
15. Hwu, J. R., Tseng, W. N., Gnabre, J., Giza, P. and Huang, R. C. C. (1998) Antiviral Activities of Methylated Nordihydroguaiaretic Acids (I) Synthesis, Structure Identification and Inhibition of Tat Regulated HIV Transactivation. *J. Med. Chem.* 41:2994–3000.
16. Chen, H., Teng, L., Li, J.-N., Park, R., Mold, D. E., Gnabre, J., Hwu, J. R., Tseng, W. N. and Huang, R. C. C. (1998) Antiviral Activities of Methylated Nordihydroguaiaretic Acids (II) Targeting Herpes Simplex Virus replication by the Mutation Insensitive Transcription Inhibitor Tetra-O-methyl-NDGA. *J. Med. Chem.* 41:3001–3007.
17. Honess, R. W., and Roizman, B. (1988) Regulation fo Herpes Virus Macromolecular Synthesis. 1. Cascade Regulation of Synthesis of Three Groups of Viral Proteins. J. Virol. 14, 8.
18. Courey, A. J., and Tjian. R. (1988) Analysis of Sp1 in vivo Reveals Multiple Transcription Domains. Including a Novel Glutamine-rich Activation Motif. *Cell* 55, 887.
19. Some of the Sp1-regulated cellular genes: Sartorelli, V.; Webster, K. A.; Kedes, L. Muscle-specif~c expresison of the cardiac alpha-actin gene requires myoD1, CarG-hox binding factor and Sp1. *Gene Dev*. 1990, 4, 181 i. Dailey, L.; Roberts, S. B.; Heintz, N. Purification of the histone H4 gene-specific transcription factors, H4TF-1 and H4TF-2. *Gene Dev.* 1988, 2, 1700. Means, A. L.; Farnham, P. J. Transcription initiation form the dihydrogolate reductase promoter is positioned by HIP-I binding at the initiation site. *Mol. Cell Biol.* 1990, 10, 653. Abravaya, K.; Phillips, B.; Morimoto, R. I. Heat shock-induced interaction so heat shock transcription factor and human hsp70 promoter examined by in vivo footprinting. *Mol. Cell Biol.* 1991, 11, 586. Leask, A.; Rosenberg, M.; Vassar, R.; Fuchs, E. Regulation fo a human epidermal keratin gene: Sequences and nuclear factors involve din keratinocyte-specific transcription. *Gene Dev.* 1990, 4, 1985. Desjardins, E.; Hay, N. Repeated CT elements bound by zinc finger proteins control the absolute and relative activities of the two principal huyman cmyc promoter. *Mol. Cell Biol.* 1993, 13, 5710. Sanchez, H. B.; Yieh, L.; Osborne, T. F. Cooperation by sterol regulatory element-binding proteins and Sp1 in sterol regulation of low-density lipoprotein receptor gene. *J. Biol. Chem.* 1995, 270, 1161. Lemaigre, F. P.; Lafontaine, D. A.; Courtois, S. J.; Durviaux, S. M.; Rousseau, G. G. Sp1 can displace GHF-1 from its distal binding site and stimulate transcription form growth hormone gene promoter. *Mol.I Cell. Biol.* 1990, 10, 1811.

20. Phelps, W. C., Yee, C. L., Munger, K. and Howley, P. M. (1988) The Human Papilloma Virus Type 16 E7 Gene Encodes Transactivation and Transformation Functions Similar to Those of Adenovirus E/A. *Cell* 53, 539–547.

21. Greenstone, H. L. Nieland, J. D., DeVisser, K. E., DeBruijn, M. L., Kimbauer, R., Roden, R. B., Lowy, D. R., Kast, W. M. and Schiller, J. T. (1998) Chimeric Papillomavirus Virus-Like particles Elicit Antitumor Immunity Against the E₇ Oncoprotein in an HPV16 Tumor Model. *PNAS* 95, 1800–1805.

22. Feltkamp, M. C., Vreugdenhil, G. R., Vierboom, M. P., Ras, E., Van der Burg, S. H., Schegget, J. Ter, Melief, C. J. M. and Kast, W. M. (1995) CTL Raised Against a Subdominant Epitope Offered as a Synthetic Peptide Eradicate Human Papillonavirus Type 16-Induced Tumors. *European Journal of Immunology* 25, 2638–2642.

23. Feltkamp, M. C., Smits, H. L., Vierboom, M. P., Minaar, R. P., B. M. Drijfhout, J. W., Schegget, J., Melief, C. and Kast, W. M. (1993) Vaccination with Cytotoxic T Lymphocyte Epitope-Containing Peptide Protects Against a Tumor Induced by Human Papillomavirus Type 16-Transformed Cells. *Eur. J. Immunol.* 23, 2242–2249.

24. Jacob, S. W. and Herschler (1986) Pharmacology of DMSO. Academic Press, Inc.

25. Jack, C., and Torre, de la (1983) Biological Actions and Medical Applications of Dimethyl Sulfoxide. New York Academy of Sciences, New York, N.Y.

26. Spruance, S. L., McKeough. M. B. and Cardinal, J. R. (1983) Dimethyl Sulfoxide as a vehicle for topical antiviral chemotherapy. *Ann. N. Y. Acad. Sci.* 411, 28–33.

27. Biswal, S. S., et al, Glutathione Oxidation and Mitochondrial Depolarization as Mechanisms of Nordihydroguaiaretic Acid-induced Apoptosis in Lipoxygenase-deficient F15.12 Cells. *Toxicol. Sci.*, 53, 77–83.(2000.)

28. Schegg, K. M. and W. J. Welch, The Effect of Nordihydroguaiaretic Acid and Related Lignans on Formyltetrahydrofolate Synthetase and Carbodylesterase. *Biochim. Biophys. Acta*, 788, 167–180.(1984.)

29. Feltkamp, M. C. W., et al., Vaccination With Cytotoxic T Lymphocyte Epitope-containing Peptide Protects Against a Tumor Induced by Human Papillomavirus Type 16-Transfromed Cells. *Eur. J. Immunol.*, 23, 2242–2249. (1993.)

30. Lin, K., et al., Treatment of Established Tumors With a Novel Vaccine That Enhances Major Histocompatiblity Class II Presentation of Tumor Antigen. *Cancer Res.*, 56, 21–26.(1996.)

31. Foley, G. E., et al., Continuous Culture of Human Lymphoblasts From Peripheral Blood of a Child With Acute Leukemia. *Cancer*, 18, 522–529.(1965.)

32. Shiebel, E., Gamma-Tubulin Complexes: Binding to the Centrosome, Regulation and Microtubule Nucleation. *Current Opinion Cellular Biology*, 12, 113–118.(2000.)

33. Marsden, M. P. F., Laemmli, U. K., Metaphase Chromosome Structure: Evidence for a Radial Loop Model. *Cell*, 17, 849–858.(1979.)

34. Taylor, W. R., et al., Mechanisms of G2 Arrest in Response to Overexpression of p53. *Molecular Biology of the Cell*, 10, 3607–3622.(1999.)

35. Innocente, S. A., et al., p53 Regulates a G2 Checkpoint Through Cyclin B1. *Proc. Natl. Acad. Sci. USA*, 96, 2147–2152.(1999.)

36. Sjottem, E.; Anderson, C.; Johansen, T. Structural and Functional Analyses of DNA Bending Induced by Sp1 Family Transcription Factors. *J.Mol. Bio.*, 1997, 267, 490–504.

37. Gnabre, J. N.; Brady, J. N.; Clanton, D. J.; Ito, Y.; Diftmer, J.; Bates, R. B.; huang, R. C. Inhibition of Human Immunodeficiency Virus Type 1 Transcription and Replication by DNA Sequence-Selective Plant Lignans. Proc. Natl. Acad. Sci. 1995, 92, 11239–11243

38. Chen, H.; Teng, L.; Li, J. N.; Park, R.; Mold, D. E.; Gnabre, J.; Hwu, J. R.; Tseng, W. N.; huang, R. C. Antiviral activities of Methylated Nordihydroguaiaretic Acids. 2. Targeting Herpes Simplex Virus Replication by the Mutation Insensitive transcription Inhibitor Tetra-O-Methyl—NDGA J. Med. Chem., 1998, 41 (16), 3001–3007.

39. Craigo, J.; Callaham, M.; Huang, R. C.; DeLucia, A. L. Inhibition of Human Padilloma virus Type Gene Expression by Nordihydroguaiaretic Acid Plant Lignan Deriuatiues Antivrral Res. 2000 In Press.

40. Hwu, J. R.; Tseng, W.n.; Gnabre, J; Giza, P.; Huang, R. C. Antiviral Activities of Methylated Nordihydroguaiaretic Acids. 1. Synthesis, Structure Identificaiton and Ibhibition of Tat-Regulated HIV Transactivation. *J.Med. Chem.*, 1998, 41 (16), 2994–3000.

41. Weislow, O. S.; Kiser, R.; Fine, D. L.; Bader, J.; Shoemaker, R. H.; Boyd, M. R. New Soluble-Formazan Assay for HIV-1 Cytopathic Effects: Application to High-Flux Screening of Synthetic and Natural Products for Aids-Antiviral Activity. *J. Natl. Cancer Inst.*, 1989, 81(8), 557–586.

What is claimed is:

1. A method for treating a tumor, said method comprising application of at least one nordihydroguaiaretic acid derivative of the formula

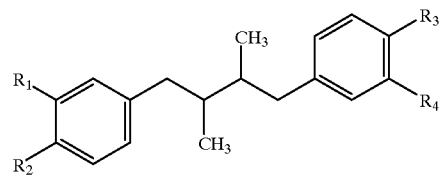

wherein $R_1$, $R_2$, $R_3$ and R4 independently represent —OH, —OCH$_3$, —O(C=O)CH$_3$, or an amino acid residue, but are not each —OH simultaneously, to said tumor.

2. The method of claim 1 wherein said tumor is cervical or oral cancer.

3. The method of claim 1 wherein said tumor is malignant.

4. The method of claim 3 wherein said tumor is selected from the group consisting of squamous cell carcinoma, adenocarcinoma and medulloblastoma.

5. The method of claim 1 wherein said tumor is benign.

6. The method of claim 5 wherein said tumor is selected from the group consisting of papilloma, teratoma and adenoma.

7. The method of claim 6 wherein said tumor is a solid tumor.

8. The method of claim 1 wherein said derivative is tetra-O-methyl nordihydroguiaretic acid ($M_4N$) or tetraglycinyl nordihydroguaiaretic acid ($G_4N$).

9. The method of claim 1 wherein tetra-O-methyl nordihydroguaiaretic acid is administered along with at least one pharmaceutically acceptable excipient or carrier.

* * * * *